(12) United States Patent
Whitehurst et al.

(10) Patent No.: US 7,904,162 B2
(45) Date of Patent: *Mar. 8, 2011

(54) MONITORING, PREVENTING, AND TREATING REJECTION OF TRANSPLANTED ORGANS

(75) Inventors: Todd K Whitehurst, Santa Clarita, CA (US); James P McGivern, Stevenson Ranch, CA (US); Kelly H McClure, Simi Valley, CA (US); Goran N Marnfeldt, Hollviken (SE); James R Thacker, Eureka, MO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 739 days.

This patent is subject to a terminal disclaimer.

(21) Appl. No.: 11/246,719

(22) Filed: Oct. 7, 2005

(65) Prior Publication Data

US 2006/0036286 A1  Feb. 16, 2006

Related U.S. Application Data

(63) Continuation of application No. 10/246,554, filed on Sep. 17, 2002, now Pat. No. 6,970,741.

(60) Provisional application No. 60/323,144, filed on Sep. 18, 2001.

(51) Int. Cl.
*A61N 1/08* (2006.01)

(52) U.S. Cl. .......................... 607/50; 607/120

(58) Field of Classification Search .............. 607/50–52, 607/120

See application file for complete search history.

(56) References Cited

U.S. PATENT DOCUMENTS

| 3,598,111 A | 8/1971 | Kahn et al. |
| 4,794,934 A | 1/1989 | Motoyama et al. |
| 5,011,472 A | 4/1991 | Aebischer et al. |
| 5,103,821 A | 4/1992 | King |
| 5,109,850 A | 5/1992 | Blanco et al. |

(Continued)

FOREIGN PATENT DOCUMENTS

WO  WO-98/37926  2/1998

(Continued)

OTHER PUBLICATIONS

Carey LC, Gunn AN, Kayser KL, Haupert AP. Influence of electrical current on renal allograft. Journal of Surgical Research; 9(1):619-622.*

(Continued)

*Primary Examiner* — Carl H. Layno
*Assistant Examiner* — Tammie K Heller
(74) *Attorney, Agent, or Firm* — Frommer Lawrence & Haug LLP; Bruce E. Black

(57) ABSTRACT

An implantable system control unit (SCU) includes means for measuring tissue impedance or other condition to determine allograft health, in order to predict or detect allograft rejection. The SCU also includes at least two electrodes coupled to means for delivering electrical stimulation to a patient within whom the device is implanted, and may also include a reservoir for holding one or more drugs and a driver means for delivering the drug(s) to the patient. In certain embodiments, the system is capable of open- and closed-loop operation. In closed-loop operation, at least one SCU includes a sensor, and the sensed condition is used to adjust stimulation parameters. Alternatively, this sensory "SCU" sounds an alarm, communicates an alarm to an external device, and/or is responsive to queries regarding sensed information, such as tissue impedance.

14 Claims, 8 Drawing Sheets

U.S. PATENT DOCUMENTS

| | | | |
|---|---|---|---|
| 5,139,028 A | 8/1992 | Steinhaus et al. | |
| 5,193,539 A | 3/1993 | Schulman et al. | |
| 5,193,540 A | 3/1993 | Schulman et al. | |
| 5,217,022 A | 6/1993 | Nathanielsz | |
| 5,246,008 A | 9/1993 | Mueller | |
| 5,282,840 A | 2/1994 | Hudrlik | |
| 5,312,439 A | 5/1994 | Loeb | |
| 5,324,316 A | 6/1994 | Schulman et al. | |
| 5,326,706 A | 7/1994 | Yland et al. | |
| 5,405,367 A | 4/1995 | Schulman et al. | |
| 5,433,735 A * | 7/1995 | Zanakis et al. | 607/50 |
| 5,447,529 A | 9/1995 | Marchlinski et al. | |
| 5,474,552 A | 12/1995 | Palti | |
| 5,562,721 A | 10/1996 | Marchlinski et al. | |
| 5,759,536 A | 6/1998 | Bellgrau et al. | |
| 5,824,029 A | 10/1998 | Weijand et al. | |
| 5,883,082 A * | 3/1999 | Bennett et al. | 514/44 A |
| 5,995,860 A | 11/1999 | Sun et al. | |
| 6,051,017 A | 4/2000 | Loeb et al. | |
| 6,122,544 A | 9/2000 | Organ | |
| 6,156,028 A * | 12/2000 | Prescott | 606/2 |
| 6,183,412 B1 | 2/2001 | Benkowski et al. | |
| 6,198,965 B1 | 3/2001 | Penner et al. | |
| 6,231,528 B1 * | 5/2001 | Kaufman et al. | 601/2 |
| 6,347,247 B1 * | 2/2002 | Dev et al. | 607/2 |
| 6,464,687 B1 | 10/2002 | Ishikawa et al. | |
| 6,671,558 B1 * | 12/2003 | Soykan et al. | 607/50 |
| 2001/0049527 A1 * | 12/2001 | Cragg | 606/61 |

FOREIGN PATENT DOCUMENTS

| | | |
|---|---|---|
| WO | WO-98/43700 | 3/1998 |
| WO | WO-98/43701 | 3/1998 |

OTHER PUBLICATIONS

Asahara, et al., "Local Delivery of Vascular Endothelial Growth Factor Accelerates Re-Endothelialization and Attenuates Intimal Hyperplasia in Balloon-Injured Rat Carotid Artery", Circulation, vol. 91, (1995), pp. 2793-2801.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Erhard, et al., "Measuring Impedance for Evaluating Ischemia Damage to the Human Liver in Preparation for Transplantation", Langenbecks Arch Chir, vol. 378(4), (1993), pp. 233-238.

Gerhausser, et al., "Diagnosis of Rejection After Kidney Transplantation by Impedance Spectroscopy with an Implantable System", Biomed Tech (Berlin), 42 Suppl, (1997), pp. 160-161.

Gersing, et al., "Measuring Electric Impedance of Organs—Methodologic Principles", Biomed Tech (Berlin), vol. 36(4), (1991), pp. 70-77.

Grauhan, et al., "Electric Myocardial Impedance Registration in Humoral Rejection After Heart Transplantation", J Heart Lung Transplant, vol. 15(2), (Feb. 1996), pp. 136-143.

Harms, et al., "Telemetric Assessment of Liver Impedance: Evaluation of a Device for the Noninvasive Diagnosis of Acute Rejection After Experimental Liver Transplantation", Biomed Tech (Berlin), vol. 45(3), (2000), pp. 43-50.

Ishikawa, et al., "Detection of Myocardial Ischemic Injury During Simple Cold Storage by Measurement of Myocardial Electrical Impedance", J Cardiovasc Surg (Torino), vol. 37(3), (Jun. 1996), pp. 261-267.

Klagsburn, M., "The Fibroblast Growth Factor Family: Structural and Biological Properties", Progress in Growth Factor Research, vol. 1, (1989), pp. 207-235.

Lopez, et al., "VEGF Administration in Chronic Myocardial Ischemia in Pigs", Cardiovasc Res, vol. 40(2), (Nov. 1998), pp. 272-281.

Pfitzmann, et al., "Intramyocardial Impedance Measurements for Diagnosis of Acute Cardiac Allograft Rejection", Annals of Thoracic Surgery, vol. 70(2), (Aug. 2000), pp. 527-532.

Sollinger, HW., "Mycophenolate Mofetil for the Prevention of Acute Rejection in Primary Cadaveric Renal Allograft Recipients", Transplantation, vol. 60, (1995), pp. 225-232.

Unger, et al., "Basic Fibroblast Growth Factor Enhances Myocardial Collateral Flow in Canine Model", American Journal of Physiology, vol. 266, (1994), pp. H1588-1595.

Vincenti, et al., "Interleukin-2-Receptor Blockade with Daclizumab to Prevent Acute Rejection in Renal Transplantation", N Engl J Med, vol. 338, (1998), pp. 161-165.

* cited by examiner

MONITORING, PREVENTING, AND TREATING REJECTION OF TRANSPLANTED ORGANS

The present application is a continuation of allowed U.S. patent application Ser. No. 10/246,554, filed Sep. 17, 2002, which application is now U.S. Pat. No. 6,970,741, issued Nov. 29, 2005, and which application claims the benefit of U.S. Provisional Patent Application Ser. No. 60/323,144, filed Sep. 18, 2001, both of which applications are incorporated herein by reference in their entireties.

FIELD OF THE INVENTION

The present invention generally relates to implantable medical systems and methods, and more particularly relates to use of implantable medical systems for monitoring, preventing, and treating rejection of transplanted organs. One or more implantable stimulators monitor the organ(s) and may alternatively or additionally apply electrical and/or drug stimulation to the transplant to aid the body's acceptance of the transplanted organ(s).

BACKGROUND OF THE INVENTION

The transplantation of healthy organs from one person to replace diseased organs in another, referred to as an allograft, has been investigated for at least a hundred years. Modern transplantation had its beginnings more than 50 years ago when it was demonstrated that allograft rejection is an immunologic event. This illustrated that successful organ transplantation would depend on attenuating or otherwise altering the immune response to the allograft.

The feasibility of solid organ transplantation was first proven with the kidney, and the seminal work in renal transplantation established the foundation necessary to proceed with all other types of solid organ transplantations. Until 1967, the kidney was the only organ allograft to be successfully transplanted in humans. In July 1967, a child's hepatoma-riddled liver was replaced with a cadaveric donor liver. Under immunosuppression with the then novel combination of azathioprine, prednisone, and antilymphoid globulin, the child survived for more than a year before dying of metastases from the primary liver cancer. Using the same anti-rejection therapy, the first successful transplantations of the human heart, lung, and pancreas were soon performed.

| First Successful Transplantation of Human Allografts (i.e., patient survival > 6 months) | | |
| --- | --- | --- |
| Organ(s) | City | Date |
| Kidney | Boston | Jan. 24, 1959 |
| Bone marrow | Paris | Apr. 23, 1963 |
| Liver | Denver | Jul. 23, 1967 |
| Heart | Cape Town | Jan. 2, 1968 |
| Lung | Ghent | Nov. 14, 1968 |
| Pancreas | Minneapolis | Jun. 3, 1969 |
| Heart-Lung | Palo Alto | Mar. 9, 1981 |
| Multiabdominal viscera | Pittsburgh | Nov. 1, 1987 |
| Small bowel segment | Cologne | Aug. 9, 1988 |
| Liver and intestine | London, Ontario | Nov. 13, 1988 |
| Total small bowel | Paris | Mar. 18, 1989 |
| Pancreatic islet | Pittsburgh | Jan. 11, 1990 |

The emergence of transplantation has paralleled the development of increasingly potent immunosuppressive agents, progressively better methods of tissue and organ preservation, refinements in tissue typing and matching, and numerous innovations in surgical techniques. These accomplishments, in combination with sweeping advances in the general care of patients (e.g., antibiotics, anesthesia, blood banking, artificial kidney and heart-lung machines), ultimately made it possible to successfully engraft all of the vital vascular organs.

In 1977, cyclosporine was shown to be immunosuppressive, and it was first used in human trials for organ transplantation in 1978. Cyclosporine was found to selectively suppress the transplant recipient's immune system, allowing the patient to tolerate the grafted organ but still thwart routine infections. FDA approval of cyclosporine in 1983 thus revolutionized organ transplantation, with greatly improved chances for long-term survival of the patient and the transplanted organ.

| Longest Living Adult Recipients | | | |
| --- | --- | --- | --- |
| Organ | Date | Patient Age | Yrs of Function |
| Kidney (LRD) | Jan. 31, 1963 | 38 | 34 yrs, 11 mo |
| Kidney (CAD) | Jan. 25, 1965 | 38 | 32 yrs, 11 mo |
| Pancreas | Dec. 3, 1980 | 25 | 17 yrs |
| Liver | Jan. 22, 1970 | 3 | 27 yrs, 11 mo |
| Heart | Apr. 4, 1975 | 28 | 22 yrs, 8 mo |
| Heart-Lung | Nov. 5, 1982 | 40 | 15 yrs, 1 mo |
| Lung (Single) | Sep. 6, 1988 | 59 | 9 yrs, 4 mo |
| Lung (Double) | Jul. 26, 1987 | 25 | 10 yrs, 5 mo |

Annually, nearly 50,000 new patients worldwide receive transplanted organs, and more than 200,000 transplant recipients in North America and Europe depend on daily cyclosporine therapy to prevent organ rejection.

Recent data indicate that, in the US, a new name is added to the United Network for Organ Sharing (UNOS) waiting list approximately every 15 minutes. Nearly 50,000 transplant procedures are performed each year throughout the world, and approximately 20,000 of these are performed in the US.

| Number of Transplants Performed in the US in 1999 | |
| --- | --- |
| Type of Transplant | Number |
| Kidney (4,153 were living donors) | 12,483 |
| Liver transplants | 4,698 |
| Pancreas alone transplants | 363 |
| Kidney-pancreas transplants | 946 |
| Intestine transplants | 70 |
| Heart transplants | 2,185 |
| Heart-lung transplants | 49 |
| Lung transplants | 885 |
| Total | 21,692 |

The current organ demand significantly exceeds the supply, as evidenced by the 40,000-plus individuals who remain untransplanted each year. In 1997 alone, 4,487 individuals in the US died while waiting for an organ. On Sep. 30, 2000, there were 72,070 individuals in the US awaiting transplantation. In an effort to increase the pool of suitable organs, researchers are experimenting with novel alternative measures such as xeno-transplantation (i.e., transplants from animals). In clinical settings, transplant surgeons are cutting adult livers in half and sewing them into children. Within three months, "cut-down" livers usually regenerate and adjust to the recipient's body. This trend is likely to continue until the shortage of organs is reversed.

Transplant Rejection

Despite chronic immunosuppressive therapy with cyclosporine and other drugs, approximately 30 percent of transplant patients experience one or more rejection episodes in the first year after surgery. These acute rejection episodes occur when T-cells recognize as foreign matter the HLA molecules on the donated organ tissue, which activates the T-cells. Once activated, these T-cells can attack and kill the foreign cells. Reversing the rejection requires a short course of powerful immunosuppressive medication, such as intensive steroid therapy. If that fails (which it does about half the time), anti-T-cell antibodies are administered. These biological agents typically are administered for 10 to 14 days, and work by binding to and destroying the patient's T-cells, thereby halting the acute rejection episode.

The first year after transplantation, the graft failure rate for kidney transplant patients is approximately 9 percent for patients whose transplant was received from a living donor, and about 19 percent for those whose transplant was cadaveric. The graft failure rate is higher for other types of organs. For kidney recipients, surgery to remove the failed organ, a return to dialysis and a possible second transplant are indicated. Failure to reverse the rejection of other transplanted organs, such as the liver or heart, often results in the death of the patient. The overall chance of surviving a liver transplant is 60-75% for adult patients and 80-90% for children.

The risk of rejection continues for the rest of the patient's life at 5 percent to 10 percent per year. At the end of 10 years, only an estimated 50 percent of organ recipients still have a functioning transplant.

Allograft rejection and its differentiation from other causes of organ dysfunction remain a diagnostic problem in transplant patients. Currently, acute rejection can be prevented by a combination of diagnostic and therapeutic modalities. Early detection requires frequent lab tests (e.g., measurement of bilirubin in the blood) and/or biopsies of the transplanted tissue.

What is needed are means and methods for detecting, preventing, and treating allograft rejection which do not have the side effects and other drawbacks of means and methods currently available.

BRIEF SUMMARY OF THE INVENTION

The invention disclosed and claimed herein addresses the above and other needs and provides systems and methods for monitoring, preventing, and/or treating a transplanted organ with at least one implantable medical device, herein called a system control unit (SCU). For instance, a miniature implantable stimulator, such as a Bionic Neuron (also referred to as a BION® microstimulator), or similar stimulator, capable of allograft monitoring by measuring electric impedance of tissue may be implanted in or adjacent a transplanted organ via a minimal surgical procedure (e.g., via a small incision and through a cannula, endoscopically, etc.). Alternatively or additionally, an implantable stimulator may apply electrical and/or drug stimulation to the transplanted organ in order to treat or prevent rejection of the organ.

According to the teachings of the present invention, the SCU monitors the impedance and impedance changes of an allograft. Immunotherapy agent(s) may be delivered by the same SCU, another SCU, or any other means of drug delivery. In addition, an SCU may includes means of delivering electrical stimulation, or an additional SCU may provide electrical stimulation. In the latter case, up to three or more SCUs may be implanted: an impedance measuring SCU, an electric stimulation SCU, and a drug delivery SCU. The means of drug delivery may include direct delivery of the drug by the SCU (i.e., without a catheter), or it may alternatively include a small catheter that is attached to the SCU. According to some teachings of the present invention, the SCU delivers electric stimulation in the form of a periodic waveform that potentiates the effects of a systemically and/or locally administered immunotherapy agent(s).

According to various embodiments of the invention, the immunotherapy agent(s) are administered systemically, and the SCU is activated at the same time or a predetermined time thereafter (e.g., ten minutes) to produce electric stimulation, and may continue to provide electric stimulation for a predetermined period following administration of the immunotherapy agent(s), e.g., two hours. According to certain embodiments of the invention, the SCU provides electric stimulation continuously, and the electric stimulation potentiates the effects of immunotherapy agents and may also provide direct effects on allograft rejection, e.g., stimulation may attenuate an immunological response. A single SCU may be implanted, or two or more SCUs may be implanted to achieve impedance monitoring, drug infusion, and/or pulses of electric current for a larger region or for a longer period of time.

According to some embodiments of the invention, the combined electric stimulation and immunotherapy is likely to cause localized attenuation of immune system activity, thereby treating patients experiencing allograft rejection and/or the symptoms thereof. Locally delivered electric current pulses delivered in synchrony with systemically and/or locally administered agents, such as methylprednisolone, dexamethosone, or other immunosuppresant(s), are likely to produce such results.

The implantable SCU capable of measuring local tissue impedance and/or supplying electric current pulses and/or drug infusion used with the present invention possesses one or more of the following properties, among other properties:

at least two electrodes for applying electrical stimulation to surrounding tissue;

a pump and at least one outlet for delivering a drug or drugs to surrounding tissue;

electronic and/or mechanical components encapsulated in a hermetic package made from biocompatible material(s);

an electrical coil or the like for receiving energy and/or information inside the package, which receives power and/or data by, for instance, inductive or radio-frequency (RF) coupling to a transmitting coil placed outside the body, thus avoiding the need for electrical leads to connect devices to a central implanted or external controller;

means for receiving and/or transmitting signals via telemetry; and means for receiving and/or storing electrical power within the SCU.

Some embodiments of the stimulator also posses one or both of the following properties:

leadless; and/or a form factor making the SCU implantable via a minimal surgical procedure (e.g., implantable via endoscopy or laparoscopy).

The size and shape of the SCU may be varied in order to deliver more effective treatment, e.g., to treat allografts of different shapes and sizes. For example, the SCU may be a thin cylindrical device with an electrode at each end, or may be a cylindrical device with multiple electrodes and/or infusion outlets along its length and/or circumference, or may be a flat circular device with two or more electrodes and/or infusion outlets distributed around its periphery, or may be a spherical device with two or more electrodes and/or infusion outlets distributed on its surface, or may have any size and configuration suitable for the particular treatment location and stimulation/infusion parameters.

An SCU may operate independently, or in a coordinated manner with other implanted SCUs, other implanted devices, and/or with devices external to the patient's body. For instance, an SCU may incorporate means for sensing a patient's condition, e.g., via a tissue impedance measurement. Sensed information may be used to control the electrical and/or drug stimulation parameters of the SCU in a closed loop manner. The sensing and electrical stimulation capabilities may be incorporated into a single SCU, the sensing and drug stimulation capabilities may be incorporated into a single SCU, and/or the sensing, electrical stimulation, and drug stimulation capabilities may all be incorporated into a single SCU. Additionally or alternatively, a sensor(s) may communicate sensed information to at least one SCU with stimulation capabilities, i.e., that can supply electric current pulses, and/or drug infusion. In some configurations, an SCU with sensing means sounds an alarm, communicates an alarm to an external device, and/or is responsive to queries regarding sensed information.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1:
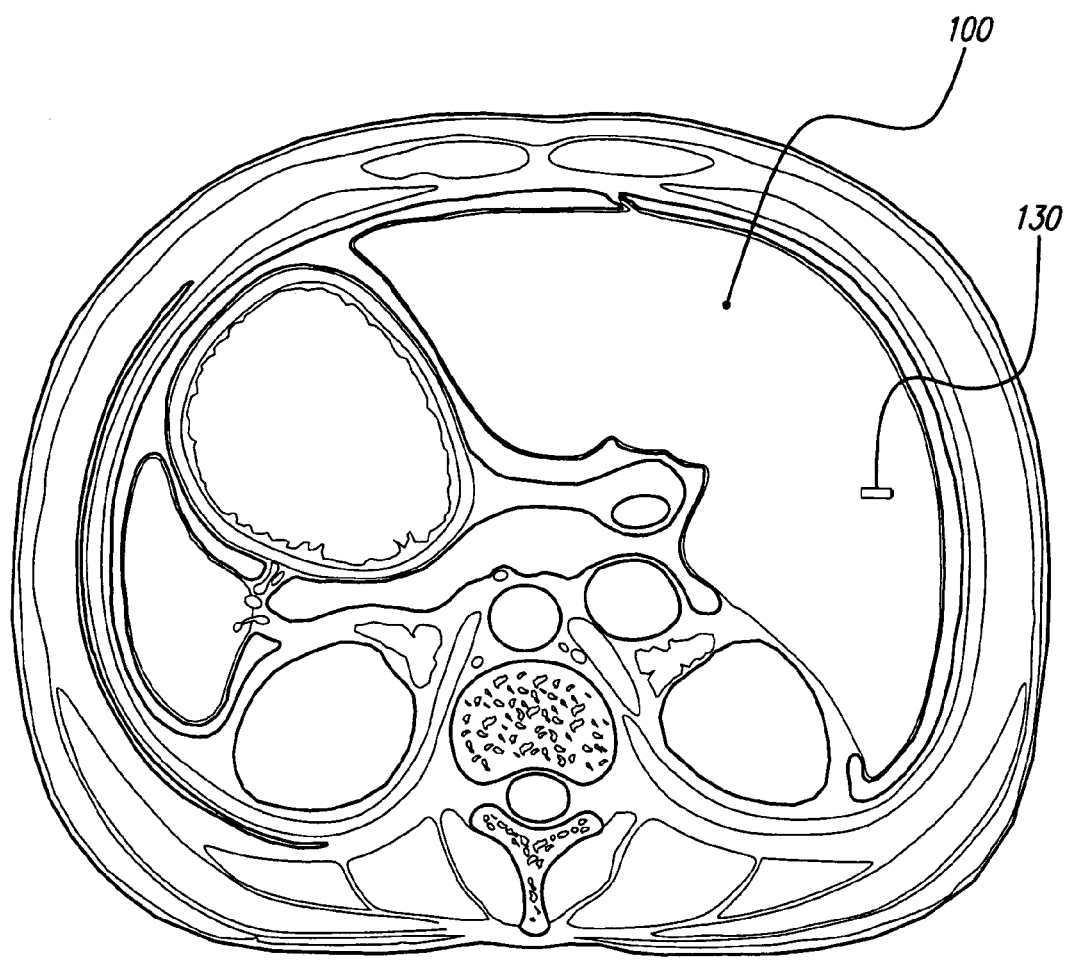
FIG. 1 is a transverse cross-section, at the level of the T12 vertebra, of the abdomen and viscera, including the liver.

The following description is of the best mode presently contemplated for carrying out the invention. This description is not to be taken in a limiting sense, but is made merely for the purpose of describing the general principles of the invention. The scope of the invention should be determined with reference to the claims.

Medication Therapy to Prevent Rejection—Immunosuppressant Drugs

Immunosuppressants are powerful drugs with many side effects and must be taken exactly as prescribed to maintain a delicate balance. Taking too little medication allows the patient's immune system to destroy the new organ. Taking too much medication alters a patient's ability to fight off an infection and increases likelihood of side effects. Taking doses too close together may cause damaging side effects.

Corticosteroids (Prednisone, etc.)

Corticosteroid immunosuppressants are used to treat a variety of diseases, including use by transplant recipients to prevent or treat rejection. Prednisone is the most commonly prescribed oral corticosteroid. Prednisone may be used in low doses for long-term immunosuppression or in higher doses for treatment of rejection. Prednisone prevents or treats rejection by suppressing the immune system. Common side effects include nausea, hyperglycemia, swelling, hypertension, mood swings, insomnia, osteoporosis, cataracts, glaucoma, corticosteroid dependency, infections, slow wound healing, bruising, rashes, and other skin changes.

Cyclosporine (Trade Names: Sandimmune® and Neoral®)

Discovered in soil fungus in 1970, cyclosporine has tremendously improved graft survival in all areas of transplantation. Neoral is a new microemulsion formulation of cyclosporine and is thought to have better absorption characteristics. As described earlier, cyclosporine prevents rejection by inhibiting T lymphocyte cells. Cyclosporine specifically blocks the signal to lymphocytes to produce IL-1, IL-2, IL-3, IL-4, and interferon gamma. Side effects include high blood pressure, kidney damage, tremors, headaches, seizures, excessive hair growth, excessive gum growth, confusion, coma, and gout. Cyclosporine is taken by mouth or given by injection.

FK506 (Tacrolimus, Prograf®)

FK506 is a derivative of a soil fungus, first described in 1987. FK506 has very similar immunosuppressive properties to cyclosporine, but is 10 to 100 times more potent on a per gram basis. Side effects include kidney damage, seizures, tremors, high blood pressure, diabetes, high blood potassium, headache, insomnia, confusion, seizures, neuropathy, and gout. FK506 is taken by mouth or given by injection.

Azathioprine (Imuran®)

Azathioprine is an immunosuppressant that may be used with other immunosuppressive medications to prevent organ rejection. Azathioprine is often prescribed so that doses of other immunosuppressant medications may be decreased and side effects may be less severe. Azathioprine is metabolized to 6-mercaptopurine, which interferes with purine synthesis and thus blocks new DNA synthesis necessary for rapidly dividing cells, i.e., it nonspecifically decreases proliferation of rapidly dividing cells. Side effects include thrombocytopenia, leukopenia, megaloblastic anemia, pancreatitis, and hepatitis. Azathioprine is taken by mouth or is given by injection.

Mycophenolate Mofetil (MMF, CellCept®, RS-61443)

In clinical studies, mycophenolate mofetil, when used in combination with cyclosporine and corticosteroids, substantially reduced the incidence of kidney rejection within the first six months following transplantation. The rate of rejection in renal allograft recipients receiving therapy with MMF is lower than during therapy with azathioprine, both given in combination with cyclosporine and corticosteroids. MMF was approved by the FDA in May 1995 for prevention of renal allograft rejection and was subsequently approved for prevention of cardiac allograft rejection. Nephrotoxicity appears to be less with MMF than with cyclosporine, and lower doses of cyclosporine can be used when mycophenolate therapy is added, thereby reducing the risk of cyclosporine-induced nephrotoxicity. Principal adverse reactions associated with the administration of MMF include diarrhea (31.0%), low white blood-cell count (23.2%), bacterial infection (13.4%), vomiting (12.5%) and a higher frequency of certain types of infections. Intravenous and oral suspensions were FDA approved in late 1998.

Daclizumab (Zenapax®) and Basiliximab

Daclizumab and basiliximab are immunosuppressants used to prevent rejection in renal allograft recipients. Daclizumab and basiliximab are monoclonal antibodies (IgG1) produced by recombinant DNA technology. Daclizumab has a longer half-life than basiliximab and is administered over a period of several weeks. The recombinant genes encoding daclizumab are a composite of human (90%) and murine (10%) antibody sequences. When used prophylactically in combination with corticosteroids and cyclosporine (with or without MMF or azathioprine), daclizumab reduces biopsy-confirmed rejection episodes in patients undergoing renal transplantation. In one study, use of daclizumab resulted in improved patient survival at one year post-transplant. Unlike muromonab-CD3, a murine monoclonal antibody, daclizumab is not indicated for the treatment of an acute rejection episode. In contrast to less specific immunosuppressants such as cyclosporine, the adverse event profile of daclizumab is comparable to that of placebo. Other potential benefits of daclizumab include lack of myelosuppression or cytokine release syndrome, no increased risk of lymphoma or other malignancies, and a lack of clinically significant drug interactions. Final FDA approval for preventing renal allograft rejection was granted December 1997. Daclizumab binds to the alpha-subunit (p55, CD25, or Tac subunit) of the interleukin (IL)-2 receptor (IL-2Ralpha). The IL-2Ralpha is only expressed on the surface of activated T-cells and is important in the clonal expansion of activated T-cells. Daclizumab inhibits binding of IL-2 to IL-2Ralpha, thus interfering with the signal that activates T-cells. Activation of lymphocytes is a critical pathway in the cellular immune response involved in allograft rejection. The effect of daclizumab differs from that of cyclosporine in that cyclosporine inhibits interleukin-2 release while daclizumab acts as an IL-2 receptor antagonist. Side effects to daclizumab are rare. Daclizumab does not appear to significantly change circulating lymphocyte numbers or cell phenotypes. Daclizumab is available as a solution (25 mg/ml) and is given intravenously.

Detection of Rejection

A number of biochemical markers may be used to detect allograft rejection. A number of these are nonspecific indicators of inflammation, e.g., white blood cell count (WBC), while a number of others are specific to the transplanted organ. For example, during liver rejection, plasma levels of liver enzymes such as aspartate transaminase (AST) and alanine aminotransferase (ALT) may be elevated. As another example, researchers have found cardiac transplant patients were at greater risk of developing coronary artery disease (the leading cause of transplant failure) when they tested positive within three months after transplant for the presence of two specific marker molecules, ICAM-1 and HLA-DR, in the inner lining of the coronary arteries. The researchers found the marker molecules during routine endomyocardial biopsy specimens performed to monitor the patients for transplant rejection. This is a potential early warning sign to physicians, as patients who developed the marker molecules in the inner lining of the coronary arteries were four times more likely than those who did not to experience transplant rejection years down the road. Early detection of transplant recipients at risk of rejection could potentially help physicians modify treatment to prevent rejection.

Detection of Rejection by Measurement of Impedance

In a recent study, Dr. J. Harms, et al., of the Technical University of Munich in Germany monitored the electric impedance in the liver following liver transplantation. They correlated the measured impedance data with biochemical and histological factors, including factors indicative of acute organ rejection. Based on the observed correlation, the researchers were able to correctly predict from electric impedance data four cases of acute rejection and 32 cases of non-rejection (p=0.004). Electrical data had an even greater correlation (r=0.84) to histological severity than most biochemical factors; only serum bilirubin and SGLDH (lactic dehydrogenase) levels proved to possess such a close correlation. The authors concluded, "[i]mpedance gradient analysis revealed evidence of a physiological relationship between liver function and the electrical properties of the organ. Telemetric impedance analysis would appear a promising means of assessing acute rejection noninvasively." [Harms, et al. "Telemetric assessment of liver impedance: Evaluation of a device for the noninvasive diagnosis of acute rejection after experimental liver transplantation." *Biomedical Engineering (Berlin)*, 2000 March; 45(3):43-50.]

In another recent study, 15 dogs received transplanted hearts and then intramyocardial impedance monitoring twice daily by means of four screw-in electrodes in the right and left ventricle. Transmyocardial biopsy and intramyocardial electrogram (IMEG) were performed to establish information about rejection. A total of 23 rejection episodes were induced. When acute rejection was recognized histologically and through IMEG readings, the animals were treated with a bolus of immunosuppressive drugs (cyclosporine and methylprednisolone) over 5 consecutive days. All hearts showed a uniform decrease in impedance of about 28.3%±5.5% immediately after transplantation, which subsequently reached a stable plateau after 7 to 8 days. Impedance values then remained unchanged as long as rejection was absent. Biopsy findings of grades 1A to 1B (ISHLT) were accompanied by a statistically significant increase in impedance of 12.2%±2.5%, of grades 2 to 3A of 19.2%±3.2%, and of grades 3B to 4 of 27.0%±2.9%. Sensitivity was 96%, and specificity was 91%. Successful treatment of rejection led to a decrease of impedance to the initial levels. The authors concluded that the amount of increase in impedance at high frequencies was a reliable method to stratify acute cardiac allograft rejection into grades similar to histological grading, and, furthermore, the effectiveness of rejection treatment can also be monitored through impedance measurement. The authors also stated, "[t]he method is also applicable for telemetric rejection monitoring by means of an implantable device." [Pfitzmann R, et al. "Intramyocardial impedance measurements for diagnosis of acute cardiac allograft rejection." *Annals of Thoracic Surgery*, 2000 August; 70(2):527-32.]

This complemented findings of researchers who, in 1996, transplanted hearts in eight dogs and monitored myocardial impedance daily by means of two intramyocardial electrodes. Day-to-day comparisons were made and an increase of electric myocardial impedance of 10% or more was used as an indicator of rejection. The authors concluded that the registration of the electric myocardial impedance diagnoses humoral rejection episodes after heart transplantation not only reliably but also early, i.e., before the onset of irreversible graft damage. [Grauhan, et al. "Electric myocardial impedance registration in humoral rejection after heart transplantation." *The Journal of Heart and Lung Transplantation*, 1996 February; 15(2): 136-43.]

Angiogenesis

When an organ is transplanted, the organ must be attached to the blood supply of the recipient. Typically, the blood supply is restored via surgical anastomosis of major vessels in the organ to the corresponding vessels in the recipient. For example, in a kidney transplant, the remaining renal artery in the donated kidney is attached to the renal artery of the recipient. However, for some organs, the blood supply may only be minimal, which may lead to poor organ function and possibly transplant rejection or failure. Treatment with agents that promote angiogenesis (i.e., the growth of new blood vessels) may thus prevent or treat organ failure or rejection due to hypoperfusion (i.e., decreased blood flow through an organ).

Recently, one of the molecular signals that initiates angiogenesis was discovered; this substance is known as vascular endothelial growth factor (VEGF). VEGF and similar compounds hold great promise angiogenesis, as VEGF can trigger and/or accelerate the growth of collateral blood vessels. In order to ensure that collateral circulation is primarily promoted in the heart, for instance, VEGF should ideally be delivered to the coronary circulation, and specifically to the artery or arteries with narrowing. VEGF may also be effective if delivered in the left atrium or ventricle, although in this case, much of the medication will be shunted to the systemic circulation.

A number of studies have shown the effectiveness of sustained intra- or extravascular administration of VEGF in chronic myocardial ischemia in improvement of left ventricular function. In 1998, Lopez, et al. extended this work by investigating the efficacy of a single bolus or local intracoronary delivery of VEGF. The left circumflex artery of 33 pigs was at least partially occluded via placement of an ameroid occluder. Three weeks later the animals were randomized to treatment with VEGF (20 mcg) by local intracoronary delivery system (n=10); by intracoronary bolus infusion (n=7); or by epicardial implantation of an osmotic delivery system (n=7) versus a control group receiving intracoronary administration of saline (n=9). After three weeks of therapy, all three VEGF treatment groups but not the control animals demonstrated a significant increase in the left-to-left (but not right-to-left) collateral index, myocardial blood flow and coronary vasodilatory reserve. The observed increase in VEGF-induced perfusion correlated with improvement in regional ventricular function in all VEGF-treated groups but not control animals. The authors conclude that a single intracoronary delivery (intravascular bolus or local delivery) of VEGF is effective in stimulating physiologically significant angiogenesis in a porcine model of chronic myocardial ischemia. [Lopez, et al. "VEGF administration in chronic myocardial ischemia in pigs." *Cardiovascular Research* 1998 November; 40(2):272-81.]

FGF (Fibroblast Growth Factor) also acts as a potent stimulator of endothelial cell proliferation. However, unlike VEGF, FGF also stimulates the proliferation of smooth muscle cells and fibroblasts. This initially raised theoretical concerns that FGF might actually lead to the enlargement of atherosclerotic plaques primarily because of its effect on smooth muscle cell proliferation. Despite this suspected drawback, FGF has proved to be just as promising an agent for therapeutic angiogenesis as VEGF. In a canine model of coronary ischemia, increased collateral circulation was observed following intracoronary injection of basic FGF (bFGF).

Therapeutic angiogenesis may also be pursued via delivery of a gene for angiogenesis. Accelerated re-endothelialization using phVEGF gene transfer, compared to recombinant VEGF protein, has been demonstrated. (phVEGF$_{165}$ is a naked plasmid DNA encoding a 165 amino acid isophorm of VEGF.) A relatively low dose of protein production as a result of gene transfection is currently believed to offer higher degrees of safety and bioactivity than the relatively large doses of recombinant protein required when VEGF is directly administered. Several gene delivery vectors are being investigated, including naked plasmid DNA and recombinant, replication-incompetent adenoviral vectors.

Figure 2:
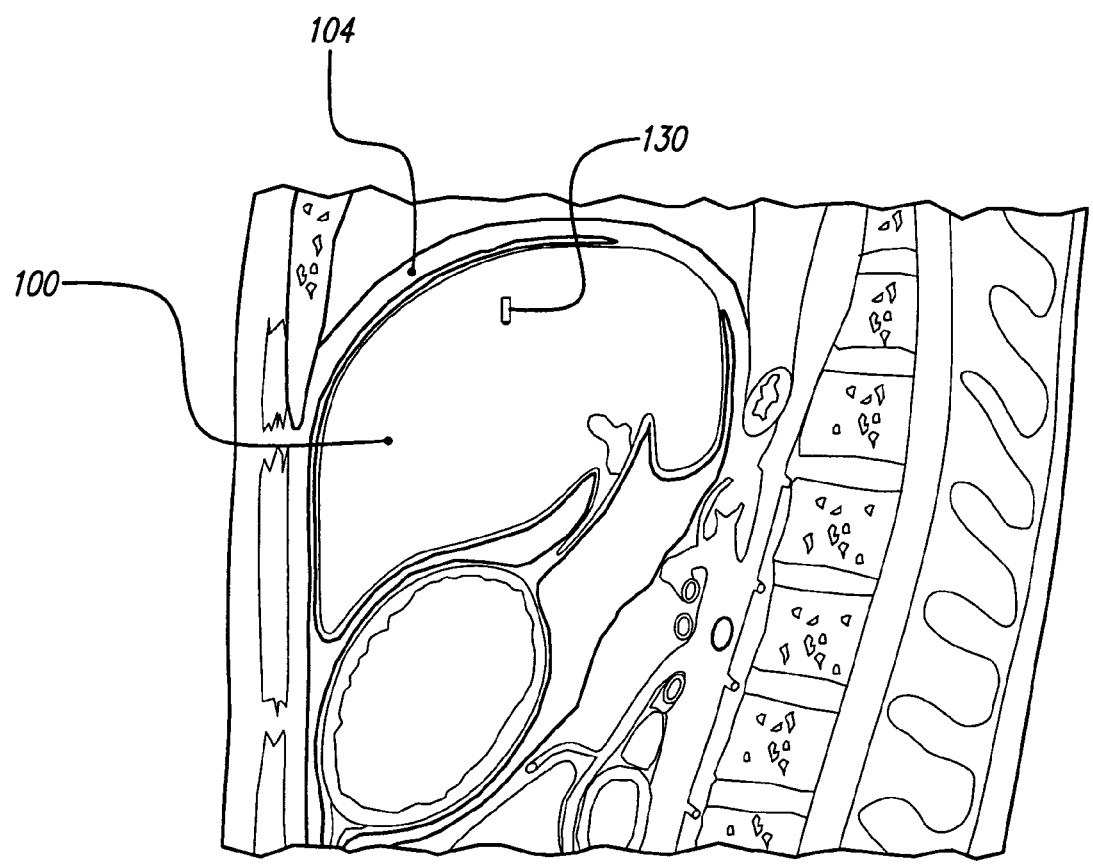
FIG. 2 is a sagittal cross-section view of the abdomen and viscera above the level of the L4 vertebra.

FIGS. 1 and 2 show a transverse cross-section view and a sagittal cross-section view, respectively, of the abdomen and viscera, including the liver. As can be seen, the liver 100 occupies the upper, right portion of the abdominal cavity, immediately below the diaphragm 104. Liver 100 will be used to demonstrate the present invention, while it is understood that the invention applies to other transplanted organs, as well.

In accordance with the teachings of the present invention and as discussed in more detail presently, measuring the impedance of an organ, such as liver 100, is provided to assess transplanted organ rejection. Monitoring of tissue impedance of a transplanted organ (i.e., allograft, xenograft (a.k.a., heterograft), or homograft) will likely be effective in indicating or predicting whether or not an organ is being rejected, thus allowing an unprecedented level of treatment of transplant rejection.

Measurement of impedance may occur by any means available for measurement of impedance, including means to measure impedance at a single frequency, as well as means to measure impedance at a spectrum of frequencies.

According to some embodiments of the invention, the stimulator applies a signal with a predetermined electric current amplitude to the tissue and measures the compliance voltage necessary to provide that current; the voltage divided by the current yields the local tissue impedance. According to certain embodiments of the invention, the stimulator applies a signal with a predetermined electric voltage amplitude to the tissue and measures the compliance current necessary to provide that voltage; again, the voltage divided by the current yields the local tissue impedance.

The stimulator may include means for communicating local tissue impedance. An alarm, or means to communicate with an external alarm device, allows the stimulator to signal, e.g., impedance outside a certain range. Further, the stimulator may include means for measuring local tissue impedance either intermittently or continuously. Continuous monitoring might allow a real-time update and display of tissue impedance.

As mentioned earlier, some embodiments of the invention include delivery of one or more drugs and/or electrical stimulation for both acute (on-demand) and traditional chronic (basal or periodic bolus) control, treatment, and/or prevention of transplant rejection. The stimulator may include the ability to apply electrical stimulation to tissue, e.g., neural tissue, muscle tissue, transplanted tissue, or other tissue. The stimulator may additionally or alternatively include the ability to apply drug stimulation to tissue, e.g., to infuse one or more drugs to the transplant, to a blood vessel(s), and/or to neural, muscle, or other tissue. Certain embodiments of the present invention also target the immunosuppressive therapy to the transplant, thereby potentially avoiding systemic side effects of traditional immunosuppressive therapy.

As used herein, "drug" comprises one or more of an immunosuppression agent(s), immunotherapy agent(s), medication(s), hormone therapy agent(s), interleukins, cytokines, lymphokines, chemokines, growth factors, synthetic or natural hormones, gene therapy agent(s), chemotherapy agent(s), and the like. As such, a stimulator may include means of delivering one or more immunosuppression agents, other drugs, or other fluids. The infusion means may include direct delivery of drug(s) by the stimulator (i.e., without a catheter), or it may alternatively include a catheter that is attached to the stimulator.

Electrical stimulation, when supplied, may take the form of a series or sequence of electrical pulses of a type typically used for stimulation of nerve or muscle tissue, such as used to treat cardiac disease. For instance, according to one alternative, the stimulation is pacemaker stimulation used to treat cardiac arrhythmias or other cardiac disease, as is familiar to those skilled in the art. According to another alternative, the stimulation is defibrillation stimulation used to treat cardiac fibrillation, also familiar to those skilled in the art.

The electrical stimulation means may be configured to operate in conjunction with any fluid infusion means of the stimulator device. Alternatively, the electrical stimulation means may operate as an alternative to any fluid infusion means. As described in more detail presently, one or more stimulators may be implanted: one or more impedance measurement "stimulators," plus possibly one or more electrical stimulators and possibly one or more drug infusion stimulators. Alternatively, a single stimulator provides impedance measurements along with one or both electrical and drug stimulation. Two of more stimulators may be implanted to achieve monitoring/treatment of a larger portion of an organ.

Small stimulators, referred to herein as "microstimulators," may be used in the methods of the invention. Other stimulators, such as an implantable signal generator(s) and electrode(s) and/or implantable pump(s) and catheter(s), as discussed in detail presently, may also be used in methods of the invention. The "stimulators" of the present invention may only monitor tissue impedance, and/or may apply electrical and/or drug stimulation to tissue, and/or may perform other sensing functions. As used herein, stimulate, stimulation, and stimulating refer to supplying electrical current pulses and/or infusion of an immunosuppression agent or other medication or stimulating drug(s). As such, electrical current parameters and/or infusion parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

The microstimulators of the present invention may be similar to or of the type referred to as BION® devices. The following documents describe various details associated with the manufacture, operation, and use of BION implantable microstimulators, and are all incorporated herein by reference:

| Application/<br>Patent/<br>Publication No. | Filing/<br>Publication<br>Date | Title |
| --- | --- | --- |
| U.S. Pat. No. 5,193,539 | Issued<br>Mar. 16, 1993 | Implantable Microstimulator |
| U.S. Pat. No. 5,193,540 | Issued<br>Mar. 16, 1993 | Structure and Method of Manufacture of an Implantable Microstimulator |
| U.S. Pat. No. 5,312,439 | Issued<br>May 17, 1994 | Implantable Device Having an Electrolytic Storage Electrode |
| U.S. Pat. No. 5,324,316 | Issued<br>Jun. 28, 1994 | Implantable Microstimulator |
| U.S. Pat. No. 5,405,367 | Issued<br>Apr. 11, 1995 | Structure and Method of Manufacture of an Implantable Microstimulator |
| PCT Publication WO 98/37926 | Published<br>Sep. 3, 1998 | Battery-Powered Patient Implantable Device |
| PCT Publication | Published | System of Implantable Devices For |

-continued

| Application/<br>Patent/<br>Publication No. | Filing/<br>Publication<br>Date | Title |
| --- | --- | --- |
| WO 98/43700 | Oct. 8, 1998 | Monitoring and/or Affecting Body Parameters |
| PCT Publication WO 98/43701 | Published<br>Oct. 8, 1998 | System of Implantable Devices For Monitoring and/or Affecting Body Parameters |
| U.S. Pat. No. 6,051,017 | Issued<br>Apr. 18, 2000<br>Published<br>September,<br>1997 | Improved Implantable Microstimulator and Systems Employing Same<br>Micromodular Implants to Provide Electrical Stimulation of Paralyzed Muscles and Limbs, by Cameron, et al., published in IEEE Transactions on Biomedical Engineering, Vol. 44, No. 9, pages 781-790. |

A BION typically produces current-controlled electrical signals, and is able to sense the voltage required to produce an electrical signal at any pre-determined current amplitude. By sensing both voltage and current, impedance may easily be determined. As will be evident to those of ordinary skill in the art upon review of the present description and of the publications listed above, the capacitive coupling normally present in the circuitry of BIONs used for neurostimulation applications may be altered by removing the capacitor attached to the stimulation electrodes, when it is desired that the BIONs measure DC impedance. Alternatively, the BION may retain its output capacitor when measuring AC impedance.

As mentioned earlier, stimulation is provided in accordance with the teachings of the present invention by electrical stimulation and/or one or more stimulating drugs. The invention includes one or more system control units (SCU) 130. In the case of electrical stimulation only, possible SCUs 130 include a microstimulator(s) and/or an implantable pulse/signal generators (IPGs). In the case of drug infusion only, an SCU 130 may comprise an implantable pump. In cases requiring both electrical stimulation and drug infusion, one or more SCUs are used. Alternatively, an SCU 130 provides both electrical stimulation and one or more stimulating drugs, and possibly also monitoring capabilities.

Figure 3A:
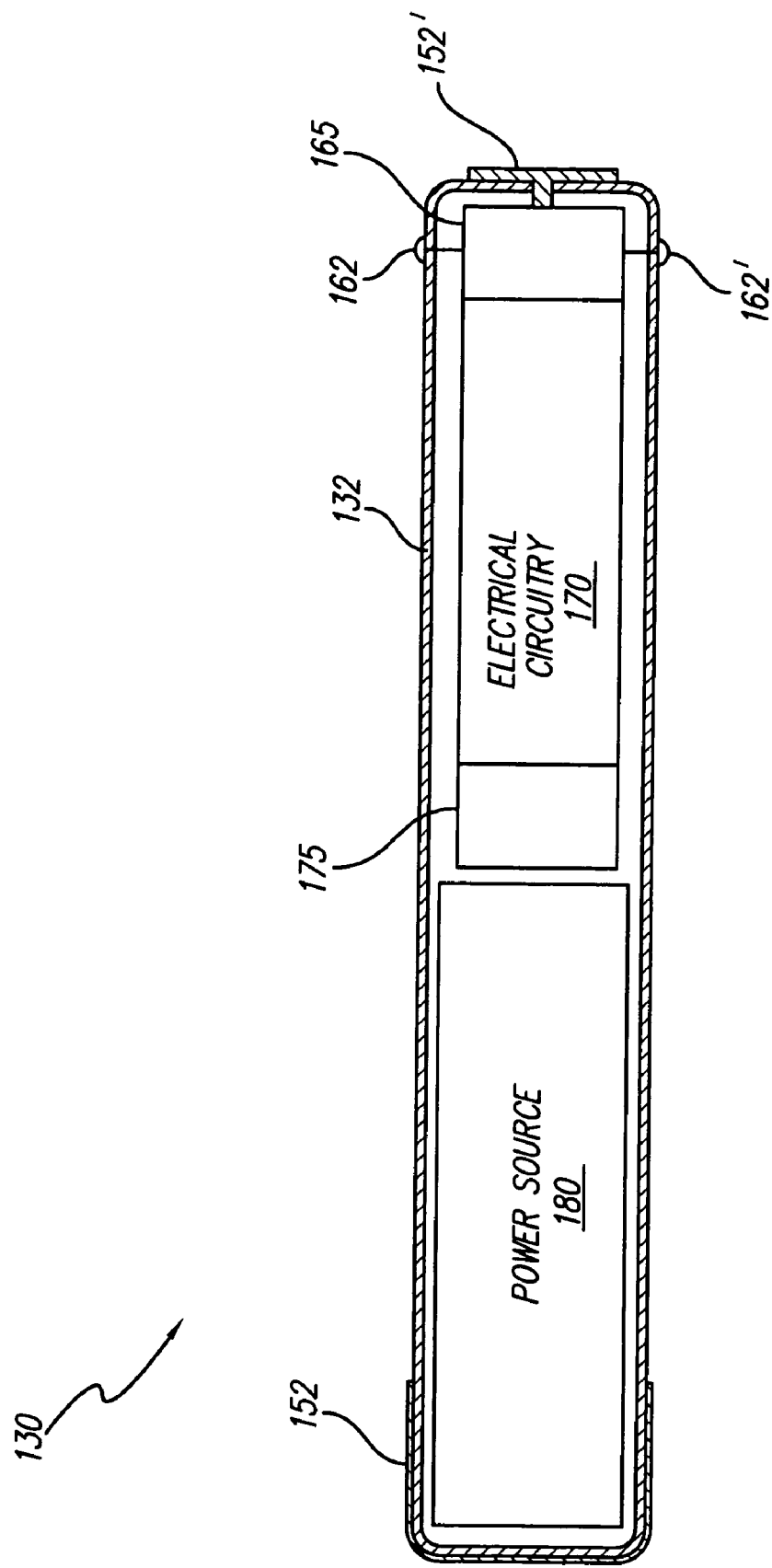
FIG. 3A is a side cross-sectional view of an exemplary embodiment of a system control unit (SCU) of the present invention.

FIG. 3A depicts a microstimulator-type SCU 130 that includes a narrow, elongated case 132 containing electrical circuitry 170 connected to electrodes 152 and 152', which may pass through the walls of the case at either end. Alternatively, electrodes 152 and/or 152' may be built into and/or onto the case and/or arranged on a catheter 160 (FIG. 3B) or at the distal portion of a lead, as described below. As detailed in the referenced publications, electrodes 152 and 152' generally comprise a stimulating electrode and an indifferent electrode (for completing the circuit). Other configurations of device 130 are possible, as is evident from the above-referenced publications, and as described in more detail herein.

Figure 3B:
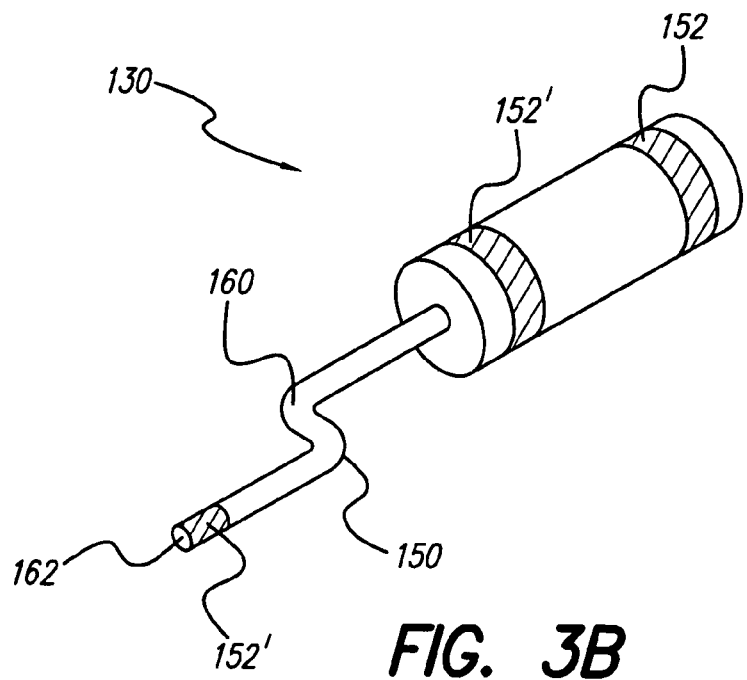
FIG. 3B is a perspective view of an SCU made in accordance with certain embodiments of the invention.
Figure 3C:
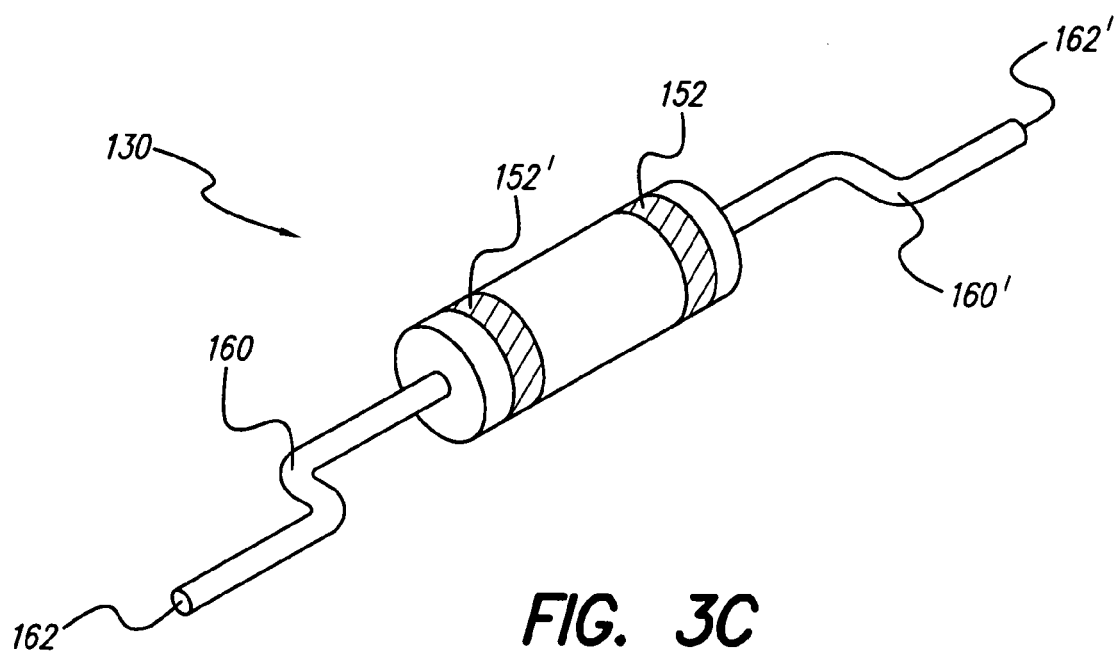
FIG. 3C is a perspective view of still another configuration of an SCU.

In the configurations depicted in FIGS. 3A-3C, SCU 130 case 152 may have a diameter of about 4-5 mm, or only about 3 mm, or even less than about 3 mm. In these configurations, SCU case length may be about 25-35 mm, or only about 20-25 mm, or even less than about 20 mm. The shape of the SCU may be determined by the structure of the desired target, the surrounding area, and the method of implantation. A thin, elongated cylinder with electrodes at the ends, as shown in FIG. 3A, is one possible configuration, but other shapes, such as rounded cylinders, spheres, disks, and helical structures, are possible, as are different configurations of and/or additional electrodes, infusion outlets, leads, and/or catheters.

In addition, the length and/or shape of an SCU 130 may be varied in order to monitor more effectively and/or deliver more effective treatment. For example, if the SCU is a thin cylindrical device with an electrode at each end, the length of this device may be varied to monitor/treat organs of different sizes. As another example, if the SCU is a flat circular (i.e., pancake-shaped) stimulator device with electrodes distributed around its periphery, the diameter of this device may be varied to treat organs of different sizes. As yet another example, the size of a substantially spherical device may be varied to treat different sizes of organs.

A microstimulator, when certain configurations are used, may be implanted with a surgical tool such as a tool specially designed for the purpose, or may be placed, for instance, via a small incision and through a small cannula. Most transplanted organs are relatively easily accessed through a percutaneous route. As such, a microstimulator may be implanted into or adjacent to a transplanted organ via a minimal surgical procedure (e.g., small incision, laparoscopically, or endoscopically). Alternatively, the device may be implanted via conventional surgical methods. A more complicated surgical procedure may be required for fixing a microstimulator in place, or when implanting microstimulators of certain shapes, or when implanting other types of stimulators. Alternatively, a stimulator may be implanted adjacent to or into a transplanted organ during the actual transplantation procedure.

In some embodiments of the instant invention, a microstimulator SCU 130 comprises at least two, leadless electrodes 152, 152'. However, one, some, or all electrodes may alternatively be located at the ends of short, flexible leads as described in U.S. patent application Ser. No. 09/624,130, filed Jul. 24, 2000, which is incorporated herein by reference in its entirety. The use of such leads permits electrical stimulation to be directed more locally to targeted tissue a short distance from the surgical fixation of the bulk of the implantable stimulator, while allowing most elements of the stimulator to be located in a more surgically convenient site. This minimizes the distance traversed and the surgical planes crossed by the device and any lead(s). In most embodiments, the leads are no longer than about 150 mm, so that the microstimulator, including any leads, may be contained entirely within the transplanted organ, e.g., liver 100, or the bulk of the stimulator may be adjacent to the organ.

SCU 130 (which herein refers to IPGs, implantable pumps, IPG/pump combinations, microstimulators for drug and/or electrical stimulation, and/or other alternative devices described herein) contains, when necessary and/or desired, electrical circuitry 170 for receiving data and/or power, from outside the body by inductive, radio frequency (RF), or other electromagnetic coupling. In certain embodiments, electrical circuitry 170 includes a power/data receiving circuit 172; an inductive coil 174 or other means for receiving and transmitting data and/or power; control circuit 171; either or both an electrical stimulation means 173, including an integrated circuit (IC) chip for decoding and/or storing stimulation parameters and generating stimulation pulses (either intermittent or continuous), and an impedance measurement means 173' that receives and processes signals from a sensor(s), such as electrodes acting as sensors; and additional discrete electronic components required to complete the electronic circuit functions, e.g., capacitor(s), resistor(s), coil(s), and the like.

Figure 3D:
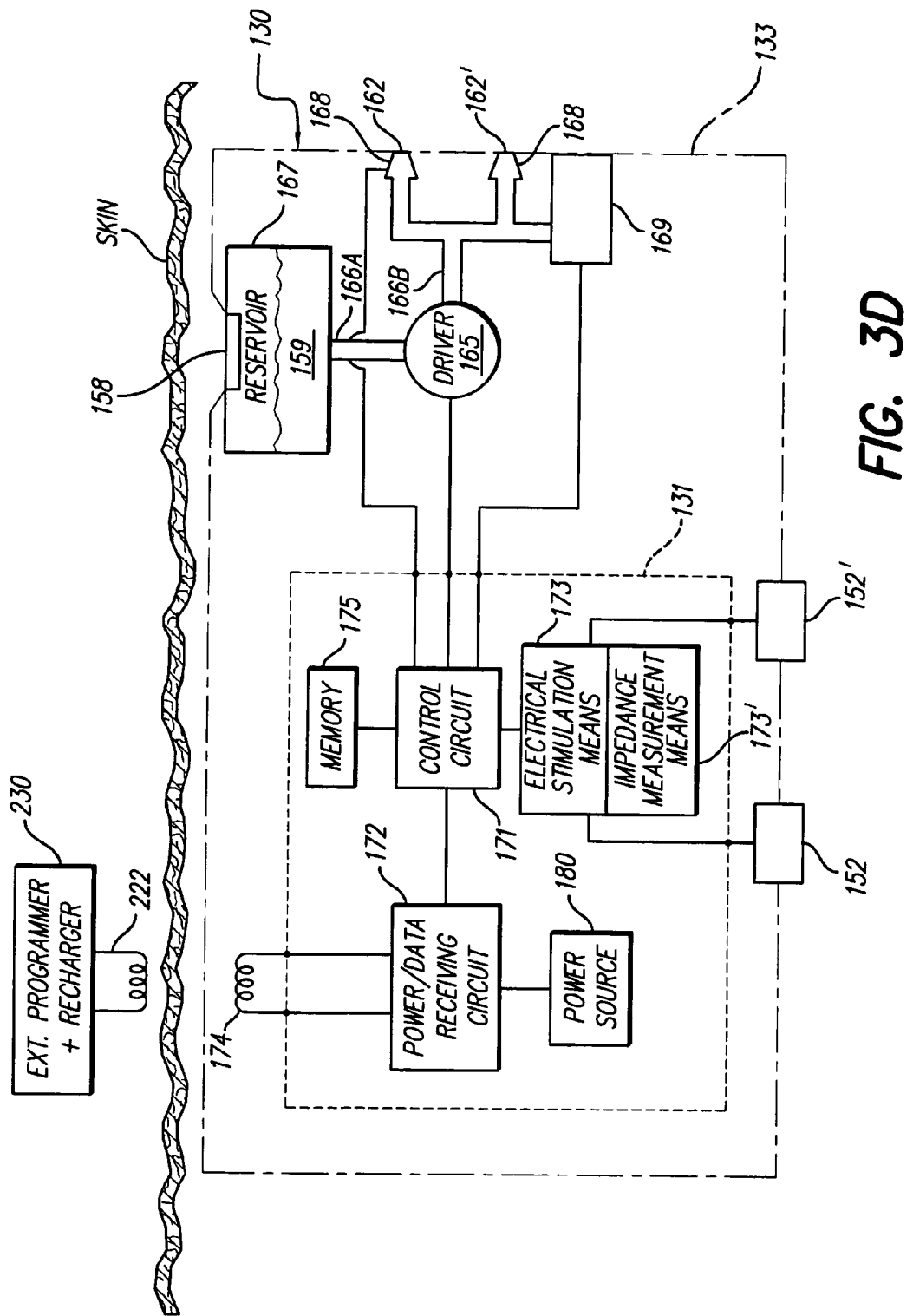
FIG. 3D is a functional block diagram of an SCU made in accordance with the invention that includes both electrical and drug stimulation capabilities.

The dashed line 131 shown in FIG. 3D represents the boundaries of an exemplary hermetically-sealed case in which at least some electrical circuitry 170 components (including a control circuit 171, a power/data receiving circuit 172, and either or both an electrical stimulation means 173, such as pulse generator circuitry, and an impedance measurement means 173'), memory 175, and power source/storage 180 are housed. The large heavy dots on line 131 represent electrical feed-through connectors that allow electrical access into hermetically-sealed case 131. The dashed-dotted line 133 represents the boundaries of the entire SCU 130, which contains other elements which may not necessarily be included within the hermetically-sealed portion 131, and may not necessarily be included in SCU 130, at all. In the case of delivering drugs with SCU 130, these optional elements may include, e.g., driver means 165 (e.g., a pump), reservoir 167 for holding drug 159, tubing 166A connecting reservoir 167 with driver means 165, and tubing 166B connecting driver means 165 with regulating means 168 and/or non-occluding means 169. Depending upon the type of driver means 165 used, portions thereof (e.g., electronic control circuits and/or elements) may also be included within the hermetically-sealed portion 131 of SCU 130.

Figure 4:
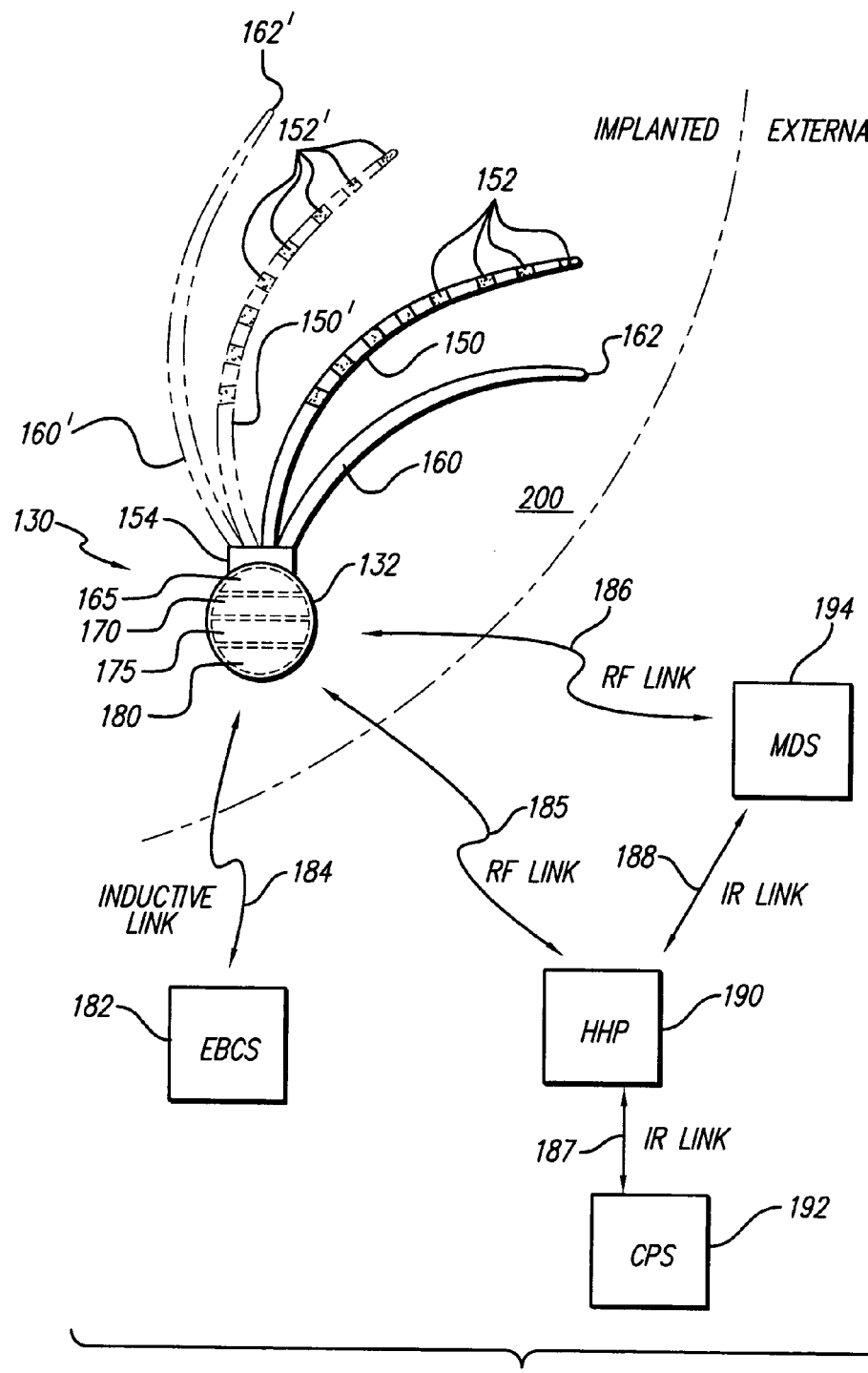
FIG. 4 illustrates internal and external components of certain embodiments of the invention.

In the embodiment of FIG. 4, an alternative SCU 130 may be implanted in a variety of locations depending on device size, and treatment location. For instance, the case 132 of SCU 130 may be implanted in the thorax or abdomen, while a lead 150 and/or catheter 160 attached to the SCU runs to the stimulation/monitoring site. Case 132 of SCU 130 may conform to the profile of surrounding tissue(s) and/or bone(s), is small and compact, and all of SCU 130 is preferably placed so as to minimize the cosmetic impact and so that no unnecessary pressure is applied to the skin or other organs or tissue, as this may result in skin erosion or infection. SCU 130 as in FIG. 4, has a diameter of about 75 mm, or only about 65 mm, or even less than about 55 mm. In these configurations, SCU thickness may be approximately 10-12 mm, or even less than about 10 mm.

The external surfaces of SCUs are advantageously composed of biocompatible materials. To protect the electrical components inside SCU 130, at least a portion of the case 132 of the SCU is hermetically sealed. For instance, SCU case 132 may be made of, for instance, glass, ceramic, or other material that provides a hermetic package that will exclude water vapor but permit passage of electromagnetic fields used to transmit data and/or power. For additional protection against, e.g. impact, the case may be made of metal (e.g. titanium) or ceramic, which materials are also, advantageously, biocompatible. In addition, SCU 130 may be configured to be Magnetic Resonance Imaging (MRI) compatible. Electrodes 152, 152' may be made of a noble or refractory metal or compound, such as platinum, iridium, tantalum, titanium, titanium nitride, niobium, or alloys of any of these, in order to avoid corrosion or electrolysis which could damage the surrounding tissues and the device.

In the case of treatment with electrical stimulation, electrode(s) 152 are carried on lead 150 having a proximal end coupled to case 132. The lead contains wires electrically connecting electrodes 152 to case 132. SCU 130 contains electrical components 170 that produce electrical stimulation pulses that travel through the wires of lead 150 and are delivered to electrodes 152, and thus to the tissue surrounding electrodes 152.

In embodiments including measurement of tissue impedance, SCU 130 contains electrical components 170 that produce signals necessary for measurement of impedance (e.g. DC voltage, AC voltage) that are delivered to electrodes 152 and/or 152', and thus to the tissue surrounding electrodes 152 and/or 152'. SCU 130 also contains electrical components 173' that sense signals necessary for measurement of impendance (e.g. DC current, AC current) that travel from the electrodes 152 and/or 152' and are delivered to electrical sensing circuits 173'.

In these tissue impedance measurement embodiments, SCU 130 includes, if necessary and/or desired, means for communicating impedance. For instance, SCU 130 may include electrical components 170 for sounding an alarm if impedance increases beyond a preset threshold. In another example, SCU 130 sends an alarm signal, e.g., via RF, to an external device. In yet another example, SCU 130 may be queried and responds with impedance information.

According to some embodiments of the invention, as depicted in FIG. 4, at least one lead 150 is attached to SCU 130, via a suitable connector 154, if necessary. Each lead includes at least two electrodes 152, and may include as many as sixteen or more electrodes 152. Additional leads 150' and/or catheter(s) 160' may be attached to SCU 130. Hence, FIG. 4 shows (in phantom lines) a second catheter 160', and a second lead 150', having electrodes 152' thereon, also attached to SCU 130. Similarly, the SCUs 130 of FIGS. 3A-3C have outlets 162, 162' for infusing a stimulating drug(s) and electrodes 152, 152' for applying electrical stimulation. In some embodiments, SCU 130 is programmable to produce either monopolar electrical stimulation, e.g., using the SCU case 132 as an indifferent electrode, or bipolar electrical stimulation, e.g., using one of the electrodes of a multi-electrode SCU as an indifferent electrode.

Lead(s) 150/150' of certain embodiments of the present invention may be less than about 5 mm in diameter, or even less than about 1.5 mm in diameter. Electrodes 152, 152' on leads 150, 150' may be arranged as an array, for instance, as two or more collinear electrodes, or even as four or more collinear electrodes, or they may not be collinear. A tip electrode may also be supplied at the distal end of one or more leads. Some configurations of SCU 130 have at least four channels and drive up to sixteen electrodes or more.

In the case of treatment alternatively or additionally constituting drug infusion, SCU 130 contains at least one driver means 165 (e.g., a pump) for storing and dispensing one or more drugs through outlet(s) 162 and/or catheter(s) 160 into a predetermined site(s). At least one septum 158, or other membrane, may be located on the surface of SCU 130 to allow transcutaneous refilling of a drug 159 by injection into an internal reservoir(s) 167 of pump 165. An SCU 130 may have exit means, such as a single exit portal 162, dual exit portal(s) 162, 162', or multiple exit portals that is/are substantially flush with the device (i.e., the device does not include a catheter, as it does in FIG. 3B) for allowing fluid egress from the device. In other configurations, the exit means includes one or more catheters 160/160'. When a catheter is used, it includes at least one outlet(s) 162/162', usually positioned at least at a distal end, while a proximal end of the catheter is connected to SCU 130. In some configurations, fluid egress occurs by passing the fluid through a membrane or a filter on the surface of the device and/or at the tip of a catheter attached to the device. In addition, catheter(s) 160/160' may have one or more electrodes 152/152' along and/or at the distal end of the catheter.

In some embodiments, SCUs of the invention include a programmable memory 175 for storing a set(s) of electrical, infusion, and/or control parameters, and/or other data, if required. This feature allows electrical, infusion, and control parameters to be adjusted to settings that are safe and efficacious with minimal discomfort for each individual. For instance, these parameters may be preprogrammed (i.e., prior to implantation), transmitted to the microstimulator after implantation, and/or controlled by a sensing device, as detailed presently.

Different stimulation parameters and/or different immunosuppression agents may have different effects on different tissues, and may thus produce different monitoring results. For example, tissue impedance is likely to vary with electrical frequency, and impedance at certain frequencies may be more indicative or predictive of organ rejection. As another example, a relatively higher amplitude applied signal may produce a different impedance measurement than a relatively lower amplitude applied signal (due to signal distortion, noise, etc.).

In addition, different stimulation parameters and different drugs may have different effects on immunosuppression and organ rejection. For instance, specific electrical parameters and/or specific infusion parameters may provide therapeutic advantages for various types and stages of organ rejection (e.g., hyper-acute rejection, acute rejection, chronic rejection). For example, some patients may respond favorably to intermittent stimulation, while others may require continuous stimulation to provide effective treatment. As another example, electric currents applied at different frequencies may have different effects on different tissues and/or with different immunotherapy agents.

Additionally, electrical, infusion and control parameters may be chosen to target specific tissues and to exclude others. For example, slow infusion rates coupled with electrical stimulation may preferentially target tissues local to infusion and/or electrical stimulation. In another example, certain immunosuppression agents may preferentially affect certain tissues and/or immune system cells. For instance, cyclosporine selectively inhibits T-cell (versus B-cell) activity.

Different infusion parameters may also have different effects on transplanted tissue. For instance, immunosuppression agents or other medications may be delivered at differing rates or with differing schedules. As another example, a relatively low infusion rate applied over a relatively long treatment period may be more effective than a relatively high infusion rate applied over a relatively short treatment period, even if the two treatments deliver the same amount of drug(s) to the tissue.

Electrical and drug stimulation parameters may be controlled independently, e.g., for continuous electrical stimulation and no drug stimulation. However, in some instances, they are advantageously coupled, e.g., electrical stimulation may be programmed to occur only during drug infusion. In addition, different combinations of synchronized electrical and infusion parameters may have different effects on transplanted tissue. For instance, some immunosuppression agents may be potentiated by a relatively low amplitude electrical stimulus applied for a relatively long time following administration, while other immunosuppression agents may be potentiated by a relatively high amplitude electrical stimulus applied for a relatively short time following administration. As another example, some combinations of electrical stimulation and immunosuppression may be appropriately applied at a steady basal rate, perhaps with periodic bolus dosing. However, it may not be necessary or desired to synchronize the electrical and infusion treatments. For instance, in some cases, the best results may be achieved by applying continuous electrical stimulation while continuously releasing an immunosuppression agent.

Some embodiments of SCU 130 also include a power source and/or power storage device 180. Possible power options for an SCU of the present invention, described in more detail below, include but are not limited to an external power source coupled to the SCU (e.g., via an RF link), a self-contained power source utilizing any suitable means of generation and/or storage of energy (e.g., a primary battery, a replenishable or rechargeable battery such as a lithium ion battery, an electrolytic capacitor, a super- or ultra-capacitor, or the like), and/or if the self-contained power source is replenishable or rechargeable, means of replenishing or recharging the power source (e.g., an RF link, an optical link, a thermal link, or other energy-coupling link).

In embodiments such as shown in FIG. 4, SCU 130 includes a rechargeable battery as a power source/storage device 180. The battery may be recharged, as required, from an external battery charging system (EBCS) 182, typically through an inductive link 184. In these embodiments, SCU 130 includes a processor and other electronic circuitry 170 that allow it to generate stimulation pulses that are applied to the patient through electrodes 152 and/or outlet(s) 162 in accordance with a program and stimulation parameters stored in programmable memory 175. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCU(s), other implanted device(s), and/or device(s) external to a patient's body, e.g., via an RF link, an ultrasonic link, a thermal link, and/or an optical link. Specifically, an SCU may communicate with an external remote control (e.g., patient and/or physician programmer) that is capable of sending commands and/or data to an SCU and that may be capable of receiving commands and/or data (e.g., impedance information) from an SCU.

For example, according to embodiments as depicted in FIG. 4, SCU 130 may be activated and deactivated, programmed and tested through a hand held programmer (HHP) 190 (which may also be referred to as a patient programmer and may be, but is not necessarily, hand held), a clinician programming system (CPS) 192 (which may also be hand held), and/or a manufacturing and diagnostic system (MDS) 194 (which may also be hand held). HHP 190 may be coupled to SCU 130 via an RF link 185. Similarly, MDS 194 may be coupled to SCU 130 via another RF link 186. In a like manner, CPS 192 may be coupled to HHP 190 via an infra-red link 187; and MDS 194 may be coupled to HHP 190 via another infra-red link 188. Other types of telecommunicative links, other than RF or infra-red may also be used for this purpose. Through these links, CPS 192, for example, may be coupled through HHP 190 to SCU 130 for programming or diagnostic purposes. MDS 194 may also be coupled to SCU 130, either directly through RF link 186, or indirectly through IR link 188, HHP 190, and/or RF link 185.

Figure 5:
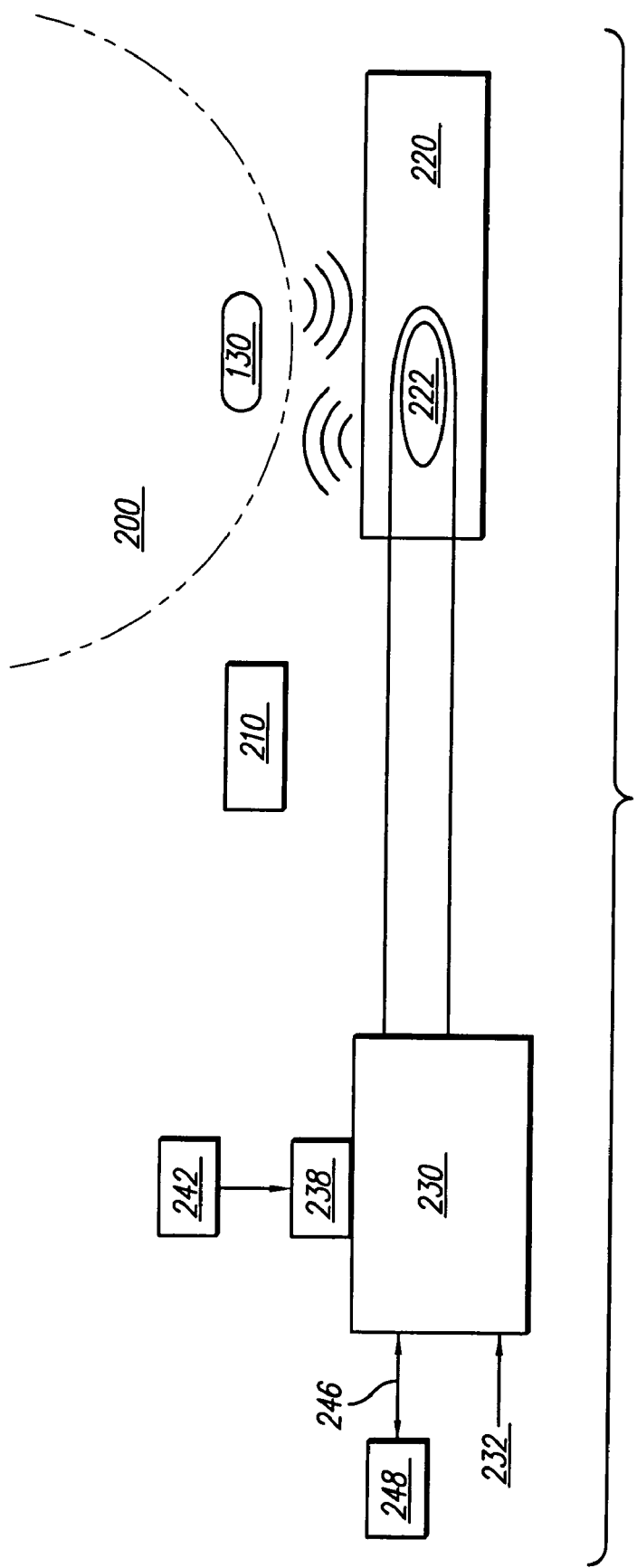
FIG. 5 illustrates additional exemplary external components of the invention.

In certain embodiments, using for example, a BION microstimulator SCU 130 as described in the above referenced patents, and as illustrated in the exemplary embodiment of FIG. 5, the patient 200 switches SCU 130 on and off by use of controller 210, which may be handheld. SCU 130 is operated by controller 210 by any of various means, including sensing the proximity of a permanent magnet located in controller 210, sensing RF transmissions from controller 210, or the like. Other methods for controlling SCU 130 are possible, such as an implanted button that may be pressed to activate SCU 130.

The embodiment of FIG. 5 also depicts exemplary external components related to programming and/or providing power to various embodiments of SCU 130. When communication with such an SCU 130 is desired, patient 200 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input device 238, e.g., a keypad, whereby the patient 200 or a caregiver 242 may request changes in measurement, electrical and/or drug stimulation, and/or control parameters produced/used during the normal operation of SCU 130. In these embodiments, manual input device 238 includes various electro-mechanical switches and/or visual display devices that provide the patient and/or caregiver with information about the status and prior programming of SCU 130.

Alternatively or additionally, external electronic appliance 230 is provided with an interface 246 for interacting with other computing devices 248, such as by a serial interface cable or infrared link to a personal computer, to a telephone modem, or the like. Such interface 246 may permit a clinician to monitor the status of the implant and prescribe new stimulation parameters from a remote location.

The external appliance(s) may be embedded in a cushion, pillow, mattress cover, or garment. Other possibilities exist, including a belt, scarf, patch, or other structure(s) that may be affixed to the patient's body or clothing. External appliances may include a package that can be, for instance, worn on the belt, may include an extension to a transmission coil affixed, for example, with a velcro band or adhesive, or may be combinations of these or other structures able to perform the functions described herein.

In order to help determine the strength and/or duration of electrical stimulation and/or the amount and/or type(s) of stimulating drug(s) required to produce the desired effect, in some embodiments, a patient's response to and/or need for treatment is sensed. For example, when electrodes and/or infusion outlet(s) of SCU 130 are implanted in or near the transplanted organ (e.g., a transplanted liver), signals from a tissue impedance measurement system built into SCU 130 may be recorded. (As used herein, "near" and "adjacent" mean as close as reasonably possible to targeted tissue, including touching or even being positioned within the tissue, but in general, may be as far as about 150 mm from the target tissue.)

An SCU may incorporate means of sensing tissue inflammation or necrosis or byproducts thereof (e.g. via a pH sensor), means of sensing tissue volume or indirect indicators thereof (e.g., via a pressure sensor), and/or may incorporate means of sensing tissue function or indirect indicators thereof (e.g., electromyograph (EMG) or electrocardiogram (ECG) changes). Other methods of determining the required electrical and/or drug stimulation include measuring levels or changes in levels of one or more neurotransmitters and/or their associated breakdown products, medications and/or other drugs, hormones, and/or any other substance(s) in the blood plasma or other bodily fluids, such as cytokines (e.g., IL-2), enzymes (e.g., AST, ALT), and/or other methods mentioned herein, and others that will be evident to those of skill in the field upon review of the present disclosure. Substances may be sensed, for instance, using one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands).

Additionally or alternatively, a patient's response to and/or need for treatment may be sensed in an immune system organ. Immune system organs, some of which are known as lymphoid organs, produce and/or regulate the white cells that are key to the immune system—lymphocytes (including B cells and T cells) and phagocytes. Immune system organs include the thymus, lymph nodes, spleen, tonsils, adenoids, appendix, bone marrow, and lymphoid tissue in the small intestine known as Peyer's patches. The blood and lymphatic vessels that transport white blood cells can also be considered immune system organs, since some immune cells, such as B cells and T cells, travel continuously throughout the body using the blood circulation and lymphatic vessels.

The sensed information may be used in a variety of ways. For instance, one or more sensors of immune system organ(s) may communicate a condition(s) to an SCU implanted in or near an allograft, and the electrical and/or drug stimulation parameters of the SCU may be adjusted accordingly, in closed-loop fashion. In other cases, the sensor(s) may be queried by an external device either automatically (e.g., on a set schedule) or manually (e.g., by a clinician during a medical visit), or the sensor(s) may automatically transmit status intermittently or continuously. In these cases, the SCU stimulation parameters may also be adjusted automatically or manually (i.e., by the patient or a caregiver using an external controller). In yet other cases, an SCU may be implanted in or near the immune system organ, and may provide electrical and/or drug stimulation to stimulate or suppress immune system function (e.g., with hormones or growth factors to stimulate white blood cell production, immunosuppressive drugs such as chemotherapy drugs to suppress white blood cell production, or the like). The stimulating SCU may also contain a sensor(s), as described below.

Yet other methods of determining a patient's response to and/or need for treatment include an iterative process whereby the physician sets stimulation levels and then adjusts them periodically based on diagnostic imaging results and/or a patient's report of symptoms, as well as other methods mentioned herein, and yet others that will be evident to those skilled in the art upon reviewing the present disclosure.

An "SCU" may additionally or alternatively incorporate means of sensing electrical current levels and/or waveforms supplied by another source of electrical energy. For instance, multiple SCUs may be placed in a patient, and one SCU may modulate its output based on the current supplied by other SCUs. Sensed information may be used to control the stimulation, measurement, and control parameters of a SCU in a closed-loop manner.

Alternatively, an "SCU" dedicated to sensory processes communicates with an SCU that provides the stimulation pulses. The implant circuitry 170 may, if necessary, amplify and transmit these sensed signals, which may be digital or analog. Alternatively, this sensory "SCU" sounds an alarm, communicates an alarm to an external device, and/or is responsive to queries regarding sensed information. Once again, the sensed information may be, but is not necessarily, used to control the stimulation, measurement, and control parameters of a SCU in a closed-loop manner.

For instance, in several embodiments of the present invention, a first and second "SCU" are provided. The second "SCU" periodically (e.g. once per minute) records tissue impedance (or pH or the level of some substance, etc.), which it transmits to the first SCU. The first SCU uses the sensed information to adjust electrical and/or drug stimulation parameters according to an algorithm programmed, e.g., by a physician. For example, the infusion rate of an immunosuppressant, e.g., a corticosteroid, may be increased in response to increased impedance. In some alternatives, one SCU performs both the sensing and stimulating functions, as discussed in more detail presently.

While an SCU 130 may also incorporate means of sensing symptoms or other prognostic or diagnostic indicators of allograft rejection, e.g., via tissue impedance measurement, it may alternatively or additionally be desirable to use a separate or specialized implantable device, such as an implantable tissue impedance sensor, to record and telemeter physiological conditions/responses in order to adjust electrical and/or drug stimulation parameters. This information may be transmitted to an external device, such as external appliance 220, or may be transmitted directly to implanted SCU(s) 130. However, in some cases, it may not be necessary or desired to include a sensing function or device, in which case stimulation parameters are determined and refined, for instance, by patient feedback.

Thus, SCU 130, or a group of two or more SCUs, may be controlled via closed-loop operation. A need for and/or response to stimulation is sensed via SCU 130, or by an additional SCU (which may or may not be dedicated to the sensing function), or by another implanted or external device. In some cases, the sensing and stimulating are performed by one SCU. If necessary, the sensed information is transmitted to SCU 130. The parameters used by SCU(s) 130 may be automatically adjusted based on the sensed information. Thus, the electrical and/or drug stimulation parameters may be adjusted in a closed-loop manner to provide stimulation tailored to the need for and/or response to the electrical and/or drug stimulation.

Figure 6:
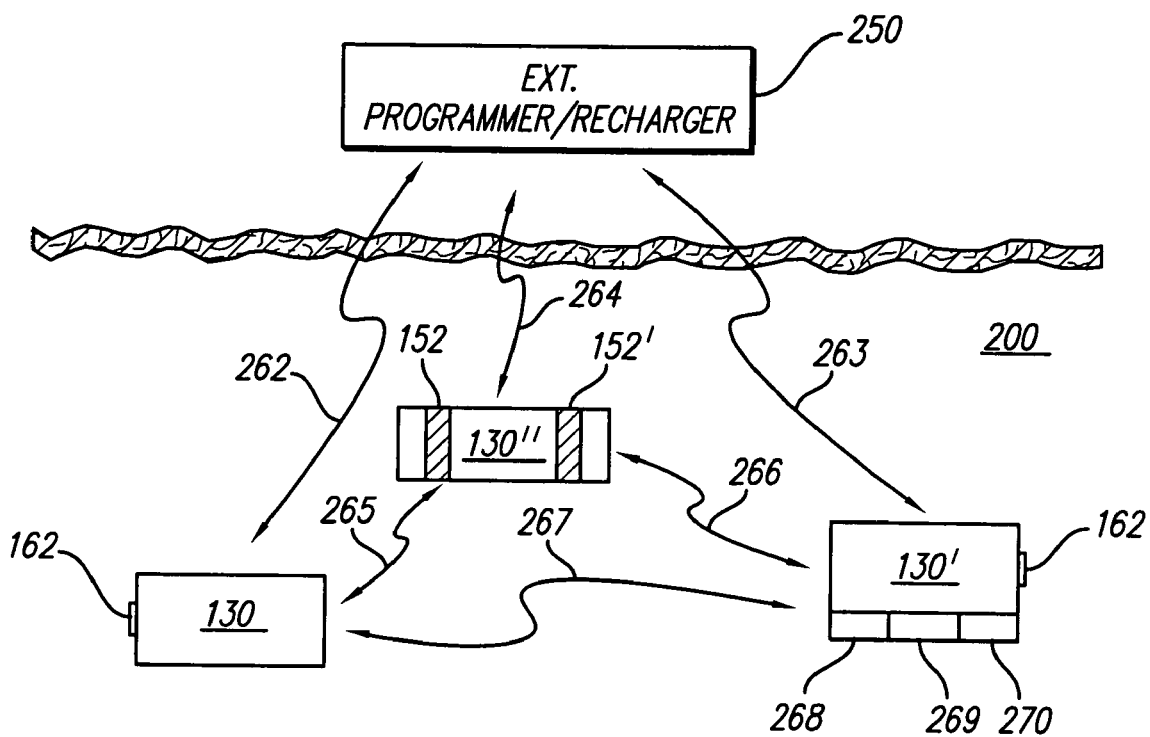
FIG. 6 depicts a system of SCUs that communicate with each other and/or with external control/programming devices to coordinate treatment.

In some embodiments, such as those comprising a microstimulator as in FIGS. 3A-3C, implantable SCU 130 is sufficiently small to permit its placement entirely within the transplanted organ, e.g., liver 100. In accordance with the present invention, a single SCU 130 may be implanted, or two or more stimulators may be implanted to achieve monitoring, drug infusion, and/or application of electric current to a larger region or for a longer period of time, as shown in FIG. 6. In FIG. 6, a first SCU 130, implanted beneath the skin of the patient 200, provides monitoring and a first drug or substance; a second implanted SCU 130' provides additional monitoring and a second drug or substance; and a third implanted SCU 130" provides electrical stimulation via electrodes 152 and 152'.

As mentioned earlier, the implanted devices may operate independently or may operate in a coordinated manner with other similar implanted devices, other implanted devices, or other devices external to the patient's body, as shown by the control lines 262, 263 and 264 in FIG. 6. That is, in accordance with some embodiments of the invention, the external controller 250 controls the operation of each of the implanted devices 130, 130' and 130". According to various embodiments of the invention, an implanted device, e.g. SCU 130, may control or operate under the control of another implanted device(s), e.g. SCU 130' and/or SCU 130". That is, a device made in accordance with the invention may communicate with other implanted stimulators, other implanted devices, and/or devices external to a patient's body, e.g., via an RF link, an ultrasonic link, or an optical link. Specifically, as illustrated in FIG. 6, SCU 130, 130', and/or 130", made in accordance with the invention, may communicate with an external remote control (e.g., patient and/or physician programmer 250) that is capable of sending commands and/or data to implanted devices and that is capable of receiving commands and/or data (e.g., sensed information) from implanted devices.

A drug infusion stimulator made in accordance with the invention may incorporate communication means for communicating with one or more external or site-specific drug delivery devices; and further has the control flexibility to synchronize and control the duration of drug delivery. The associated drug delivery device typically provides a feedback signal that lets the control device know it has received and understood commands. The communication signal between the implanted stimulator and the drug delivery device is encoded to prevent the accidental or inadvertent delivery of drugs by other signals.

An SCU made in accordance with the invention further incorporates, in certain embodiments, first sensing means 268 for sensing therapeutic effects, clinical variables, or other indicators of the state of the patient, such as changes in tissue impedance resulting from changes in the condition of the allograft. The SCU additionally or alternatively incorporates second sensing means 269 for sensing pH, oxygen levels, neurotransmitter levels and/or their associated breakdown product levels, medication levels and/or other drug levels, hormone, enzyme, interleukin, cytokine, lymphokine, chemokine, and/or growth factor levels and/or changes in these or other substances in the blood plasma or local interstitial fluid. The SCU additionally or alternatively incorporates third sensing means 270 for sensing electrical current levels and waveforms supplied by another source of electrical energy. Sensed information may then be used to control the infusion and/or electrical parameters of the stimulator(s) in a closed loop manner, as shown by control lines 266, 267, and 265, and/or by an external device(s), as shown by control lines 262, 263, and 264.

According to one alternative, the impedance monitoring, other sensing, electrical, and drug stimulating means are all incorporated into a single SCU. According to other alternatives, only one or only some of these capabilities are incorporated into a single SCU. For example, an SCU may incorporate impedance monitoring and electrical stimulation only. In another example, a SCU may incorporate impedance monitoring, electrical stimulation, and sensing. In another alternative, the sensing means are incorporated into at least one "SCU" (that may or may not have stimulating or impedance monitoring means), and the sensed information is communicated to at least one other SCU with stimulating and/or impedance monitoring means. The implant circuitry 170 amplifies and transmits these sensed signals, if necessary, which may be analog or digital. Sensed information sensed by the sensing means may then be used to control the electrical, infusion, and/or control parameters in a closed-loop manner.

Thus, it is seen that in accordance with the present invention, and as depicted in FIG. 5, one or more external appliances may be provided to interact with SCU 130, and may be used to accomplish, potentially among other things, one or more of the following functions:

Function 1: If necessary, transmit electrical power from the external electronic appliance 230 via appliance 220 to SCU 130 in order to power the device and/or recharge the power source/storage device 180. External electronic appliance 230 may include an automatic algorithm that adjusts stimulation parameters automatically whenever the SCU(s) 130 is/are recharged.

Function 2: Transmit data from the external appliance 230 via the external appliance 220 to SCU 130 in order to change the parameters (e.g., electrical and/or drug stimulation parameters) used by SCU 130.

Function 3: Transmit sensed data indicating a need for treatment or in response to stimulation from SCU 130 (e.g., impedance, change in pH, medication level, or other activity) to external appliance 230 via external appliance 220.

Function 4: Transmit data indicating state of the SCU 130 (e.g., battery level, drug level, stimulation parameters, etc.) to external appliance 230 via external appliance 220.

By way of example, a treatment modality for liver transplant rejection monitoring, prevention, and treatment is carried out according to the following sequence of procedures:

1. An SCU 130 is implanted so that it is entirely within liver 100. If necessary or desired, one or more additional stimulator(s) 150 may be implanted in other areas in or near liver 100, such as at a location adjacent to a major blood vessel feeding the liver. In another alternative, the electrodes of a lead and/or the output portion of a catheter(s) are implanted in liver 100, while the bulk of the SCU 130 (i.e., case 132) is implanted a short distance away, e.g., in the abdomen.
2. Using Function 2 described above (i.e., transmitting data) of external appliance 230 and external appliance 220, SCU 130 is commanded to periodically infuse an immunotherapy agent(s) and to produce electric stimulation pulses during and/or for a time period after infusion.
3. Set stimulator on/off period(s) to an appropriate setting(s), e.g., one hour on followed by three hours off for both electrical and drug stimulation. As another example, set infusion for one hour on, then three hours off, while electrical stimulation is set to three hours on, then one hour off.
4. At some predefined interval, any change in impedance, pH, and/or oxygen level is sensed, for instance, by one or more electrodes 152 and 152' or sensors 268, 269, 270. These responses are converted to data and telemetered out to external electronic appliance 230 via Function 3. Alternatively, after an initial treatment period (e.g., one month), allograft condition may be assessed by, for example, report of symptoms, biopsy, ultrasound imaging, CT imaging, and/or other diagnostic imaging.
5. From the response data received at external appliance 230 from SCU 130, or from other assessment, the threshold for obtaining a response is determined and is used by a clinician 242 acting directly 238 or by other computing means 248 to transmit the desired electrical and/or drug stimulation parameters to SCU 130 in accordance with Function 2. For instance, if allograft rejection is detected by impedance monitoring, via biopsy, or on a CT scan image, infusion rate(s) and/or on periods may be increased, and/or electrical stimulation on period(s) may be increased.
6. To cease treatment, controller 210 may be employed to turn off SCU 130.
7. Periodically, the patient or caregiver recharges the power source/storage device 180 of SCU 130, if necessary, in accordance with Function 1 described above (i.e., transmit electrical power).
8. Periodically, reservoir 167 of SCU 130 is refilled with the appropriate drug(s).

For the treatment of any of the various locations and types of allograft and degrees of allograft rejection, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 130, each of which could be separately controlled by means of a digital address. Multiple channels and/or multiple patterns of electrical and/or drug stimulation might thereby be programmed by the clinician and controlled by the patient in order to, for instance, stimulate larger areas of an organ in order to maximize therapeutic efficacy.

According to one alternative, the SCU receives a signal from an external device, measures local tissue impedance (or lymphocyte levels/changes in an immune system organ, or some other measure(s) in an allograft or immune system organ) in response, and communicates the measured impedance data (e.g., transmits it in an encoded format) to an external device. According to another alternative, the SCU periodically measures local tissue impedance and communicates it to an external device; the period of communication may be hard-wired, responsive to a measurement, or may be programmed by an external device. According to another alternative, the SCU periodically measures local tissue impedance and stores the impedance data along with a relative or absolute indicator of when the measurement occurred. When the SCU receives a signal from an external device, it communicates the stored impedance data (possibly transmitted in encoded form) to an external device, at which point it may or may not clear its memory.

Thus, according to certain embodiments of the invention, if monitoring indicates impending or current organ rejection, one or more immunosuppression agents are administered, and at the same time, the SCU(s) may be activated to produce electrical stimulation. The SCU(s) may continue to provide electrical stimulation for a predetermined period following the administration of the immunosuppression agent(s), e.g., 2 hours. This may provide benefits for patients, such as continuing to cause selective uptake of immunosuppression agents even after administration has ceased, and/or providing benefits of immunosuppression even at normally sub-therapeutic levels. According to various embodiments of the invention, the SCU(s) provide electrical stimulation continuously, and the electrical stimulation may both potentiate the effects of immunosuppression agents and may also provide direct effects on organ rejection.

Immunosuppression therapy may be carried out by delivery of one or more of any known medications or other substance known to suppress allograft rejection. Such medications may include any corticosteroid (e.g., methylprednisolone, dexamethasone), cyclosporine, FK506, azathioprine, mycophenolate mofetil, daclizumab, basiliximab, and/or nicotine receptor agonist (NRA). Such drugs may also include genes or gene products that lead to suppression of allograft rejection, e.g., genes that suppress expression of cell antigens in an allograft that lead to an immune attack.

In some embodiments of the invention, immunosuppression therapy is carried out chronically through a basal rate and/or periodic bolus delivery of an immunosuppressant(s). The parameters of delivery may be constant or may be modulated by a physician, a patient, or other caregiver. The parameters of delivery may also be modulated by sensed data or by another device(s), as discussed earlier.

In various embodiments of the invention, delivery of an immunosuppressant(s) may be increased during an episode of acute allograft rejection. Such an increase may reflect an increase in basal rate and/or an increase in bolus dose and/or rate. This increase in delivery may be initiated by a physician, a patient, or other caregiver. This increase in delivery may additionally or alternatively be initiated by sensed data or by another device(s), as discussed earlier. During acute allograft rejection, certain immunosuppressive agents that are not normally infused may additionally be infused.

Target sites for drug infusion include any of the vessels that feed an allograft, e.g., the coronary arteries in a cardiac transplant or the renal arteries in a kidney transplant. Such vessels must be anastomosed during transplant surgery, which may offer an opportune time to implant the SCU 130 and/or catheter(s) 160. Targeted drug infusion is likely to avoid some of the systemic side effects seen with systemic immunosuppressants. Such targeted delivery is likely to work well for some drugs, e.g., corticosteroids, but may be less advantageous or desirable for other drugs.

Additional target sites for drug infusion include any other blood vessel, if immunosuppression therapy is delivered systemically. A blood vessel that is unlikely to suffer significant trauma with implantation or attachment of a chronic infusion catheter (e.g., inferior vena cava) may be most appropriate in the case of systemic therapy.

As mentioned earlier, some embodiments of this invention use one or more drugs to treat and prevent allograft rejection chronically. According to various embodiments of the invention, one or more of the infused drugs is a medication used for chronic treatment of allograft rejection, such as any corticosteroid (e.g., methylprednisolone, dexamethasone), cyclosporine, FK506, azathioprine, mycophenolate mofetil, daclizumab, basiliximab, and/or nicotine receptor agonist (NRA). Such drugs may also include genes or gene products that lead to suppression of allograft rejection, e.g., genes that suppress expression of cell antigens in an allograft that lead to an immune attack. Such chronic medication or gene therapy may be delivered at a basal rate or via periodic bolus, as programmed by a physician. The dosage may also be programmed by a clinician. If an SCU has sensing capability or interfaces with other devices that have sensing capability, such chronic medication delivery may modulated by information sensed by the SCU or transmitted to the SCU. For example, the infusion rate of corticosteroids might be modulated by a sensor that senses plasma corticosteroid level or tissue impedance.

Certain embodiments of this invention additionally or alternatively use one or more drugs to deliver immunosuppression therapy acutely. According to various embodiments, one or more of the infused drugs is a medication used for acute treatment and prevention of allograft rejection, such as high-dose corticosteroids. Such acute medication may be delivered on demand when the patient indicates such delivery is required, such as via depression of an implanted button or via a remote control that is in communication with the SCU. The control algorithm and/or dosage may be programmed by a clinician. If an SCU has sensing capability or interfaces with other devices that have sensing capability, such acute medication may alternatively be delivered when the SCU senses or is informed of acute allograft rejection. For example, high-dose corticosteroids might be delivered by the SCU when it senses a significant increase in allograft tissue impedance. As another example, high-dose corticosteroids might be delivered by the SCU when it senses T wave inversion and ST elevation on the ECG of a transplanted heart, indicating possible coronary artery occlusion or other cardiac dysfunction due to acute allograft rejection.

Additional embodiments of this invention also use one or more angiogenesis drugs to prevent and/or treat allograft ischemia or rejection. According to some embodiments of the invention, one or more of the infused drugs is a medication used to promote angiogenesis, such as VEGF or FGF. According to other embodiments of the invention, one or more of the infused substances is a gene that encodes a protein or other gene product that leads to angiogenesis, such as phVEGF. Such an agent(s) to promote angiogenesis may be delivered at a basal rate or via periodic bolus, as programmed by a physician. The dosage or amount delivered may also be programmed by a clinician. If an SCU has sensing capability or interfaces with other devices that have sensing capability, such chronic angiogenesis drug or gene delivery may modulated by information sensed by the SCU or transmitted to the SCU. For example, the infusion rate of VEGF might be modulated by a sensor that senses tissue or plasma oxygenation. In some embodiments, the SCU has a size and shape suitable for placement entirely within the neoplasm of the allograft and for implantation via a cannula.

According to some embodiments of the invention, the SCU delivers electric stimulation in the form of a periodic waveform that locally potentiates the effects of a systemically and/or locally administered immunotherapy agent(s). The immunotherapy agent(s) may be delivered by the same SCU, another SCU, or any other means of drug delivery. The electric stimulation is likely to cause increased perfusion and increased cell activity and consequent increased cellular uptake of the locally delivered immunotherapy agent(s), thereby treating allograft rejection and/or the symptoms thereof. Locally delivered electric current pulses (e.g., about 0.1-10 mA, 1-100 Hz) delivered in synchrony with systemically and/or locally administered immunosuppressive agents, e.g., a corticosteroid such as methylprednisolone or dexamethasone, are likely to produce such results.

Additionally, sensing means described earlier may be used to orchestrate first the activation of SCU(s) targeting one area of an allograft, and then, when appropriate, the SCU(s) targeting the same or another area of the allograft, in order to control symptoms, for instance, by a different means. Alternatively, this orchestration may be programmed, and not based on a sensed condition.

Additional uses of the present invention include measurement of changes in electrical impedance of a transplant organ during storage, prior to implant, which may be a reliable indicator of graft viability during preservation of an organ transplant.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with an allograft, comprising:
   providing a system control unit, wherein the system control unit comprises a power source disposed within a housing;
   implanting the system control unit in or near an allograft, wherein the allograft is an organ from another person that is transplanted into the patient;
   providing operating power to the system control unit;
   providing stimulation parameters to the system control unit; and
   delivering stimulation with the system control unit to allograft tissue adjacent to the system control unit according to the stimulation parameters thereby preventing or reducing rejection of the transplanted organ by the patient's body;
   wherein the stimulation comprises both electrical stimulation and stimulation via at least one drug, and wherein the drug and the electrical stimulation are delivered by the system control unit.

2. The method of claim 1, wherein the system control unit has a size and shape suitable for placement entirely within the allograft and wherein implanting the system control unit comprises implanting the system control unit via a cannula.

3. The method of claim 1, wherein the at least one drug delivered to the allograft is at least one of a corticosteroid, cyclosporine, FK506, azathioprine, mycophenolate mofetil, daclizumab, and basiliximab.

4. The method of claim 1, further comprising:
   providing at least one sensor;
   using the sensor to sense a physical condition;
   determining the stimulation parameters based at least in part upon the sensed physical condition.

5. The method of claim 4, wherein the at least one sensor is a part of the system control unit.

6. The method of claim 4, wherein the sensed physical condition includes level or change in level of at least one of an electric impedance of the transplanted organ, inflammation of the transplanted organ, and necrosis of the transplanted organ.

7. The method of claim 4, wherein the sensed physical condition includes level or change in level of at least one of tissue volume, pressure, oxygen, or pH or change in an EMG, or ECG.

8. The method of claim 1, further comprising using at least one external appliance to determine the stimulation parameters.

9. The method of claim 1, wherein the stimulation parameters are determined by the at least one system control unit.

10. The method of claim 1, further comprising providing and implanting more than one system control unit.

11. The method of claim 1, further comprising opening an implantation site before implanting the system control unit and closing the implantation site after implanting the system control unit, wherein the system control unit remains implanted in or near the allograft after closing the implantation site.

12. The method of claim 1, wherein the at least one drug delivered to the allograft is at least one of a nicotine receptor agonist, a gene that leads to suppression of allograft rejection, a gene product that leads to suppression of allograft rejection, a medication used to promote angiogenesis, a gene that encodes a protein that leads to angiogenesis, a gene product that leads to angiogenesis, VEGF, FGF, and phVEGF.

13. The method of claim 1, wherein implanting the system control unit in or near an allograft comprises implanting the system control unit during an organ transplantation procedure.

14. The method of claim 1, wherein the organ from another person that is transplanted into the patient comprises a liver, a kidney, a lung, an intestine or a pancreas.

* * * * *